United States Patent
Davis et al.

(10) Patent No.: US 10,773,067 B2
(45) Date of Patent: Sep. 15, 2020

(54) ENTERAL CONNECTORS HAVING COUPLING FEATURES

(71) Applicant: NEOMED, INC., Woodstock, GA (US)

(72) Inventors: Benjamin Martin Davis, Woodstock, GA (US); Aaron N. Ingram, Canton, GA (US); Mariann Cary, Canton, GA (US); Mark M. Costello, County Mayo (IE); Tony Doherty, County Mayo (IE); Adrian McDermott, County Galway (IE)

(73) Assignee: NeoMed, Inc., Woodstock, GA (US)

( * ) Notice: Subject to any disclaimer, the term of this patent is extended or adjusted under 35 U.S.C. 154(b) by 590 days.

(21) Appl. No.: 15/454,761

(22) Filed: Mar. 9, 2017

(65) Prior Publication Data

US 2017/0173321 A1    Jun. 22, 2017

Related U.S. Application Data

(63) Continuation-in-part of application No. 15/185,583, filed on Jun. 17, 2016, now Pat. No. 10,576,020, and
(Continued)

(51) Int. Cl.
*A61M 39/10* (2006.01)
*A61M 39/20* (2006.01)
*A61M 5/31* (2006.01)

(52) U.S. Cl.
CPC .......... *A61M 39/10* (2013.01); *A61M 5/3134* (2013.01); *A61M 39/20* (2013.01);
(Continued)

(58) Field of Classification Search
CPC .. A61M 2005/3104; A61M 2005/3106; A61M 5/3202; A61M 5/3134; A61M 2005/312; B65D 41/17
See application file for complete search history.

(56) References Cited

U.S. PATENT DOCUMENTS

| 1,970,631 A | * | 8/1934 | Sherman | ................ | B65D 41/04 |
| | | | | | 222/498 |
| 2,477,598 A | | 8/1949 | Hain | | |

(Continued)

FOREIGN PATENT DOCUMENTS

| DE | 7740288 U1 | 5/1978 |
| DE | 8613738 U1 | 7/1986 |

(Continued)

OTHER PUBLICATIONS

Alternative Syringes Low Displacement Option PowerPoint Presention; Presented by Rork Swisher of Covidien; ISO 30369 Series Meeting; Berlin Germany; 11 pgs; Mar. 19, 2014.
(Continued)

*Primary Examiner* — Jason E Flick
*Assistant Examiner* — Tasnim Mehjabin Ahmed
(74) *Attorney, Agent, or Firm* — Dority & Manning, P.A.

(57) ABSTRACT

Enteral connectors having coupling features for providing removable or permanent coupling engagement with a syringe connector. In some example embodiments, the syringe connector includes an ENFit compatible female connector. In other example embodiments, the syringe connector includes a threaded tip.

19 Claims, 18 Drawing Sheets

Related U.S. Application Data a continuation-in-part of application No. 15/078,674, filed on Mar. 23, 2016, now Pat. No. 10,624,816, and a continuation-in-part of application No. 14/844,922, filed on Sep. 3, 2015.

(60) Provisional application No. 62/192,726, filed on Jul. 15, 2015, provisional application No. 62/192,618, filed on Jul. 15, 2015, provisional application No. 62/181,595, filed on Jun. 18, 2015, provisional application No. 62/174,289, filed on Jun. 11, 2015, provisional application No. 62/138,156, filed on Mar. 25, 2015, provisional application No. 62/137,293, filed on Mar. 24, 2015, provisional application No. 62/047,364, filed on Sep. 8, 2014.

(52) U.S. Cl.
CPC ........... A61M 2005/312 (2013.01); A61M 2005/3104 (2013.01); A61M 2039/1033 (2013.01); A61M 2205/586 (2013.01)

(56) References Cited

U.S. PATENT DOCUMENTS

| | | |
|---|---|---|
| 3,307,752 A | 3/1967 | Anderson |
| 3,344,786 A | 10/1967 | Berg et al. |
| 3,468,309 A | 9/1969 | Drewe |
| 3,473,833 A | 10/1969 | Bremer |
| 3,572,337 A | 3/1971 | Schunk |
| 3,712,749 A | 1/1973 | Roberts |
| 3,937,211 A | 2/1976 | Merten |
| 4,043,334 A | 8/1977 | Brown et al. |
| 4,046,145 A | 9/1977 | Choksi et al. |
| 4,286,591 A | 9/1981 | Raines |
| 4,685,173 A | 8/1987 | Pavur |
| 4,717,386 A | 1/1988 | Simmons |
| 4,743,229 A | 5/1988 | Chu |
| 4,842,592 A | 6/1989 | Caggiani et al. |
| D303,710 S | 9/1989 | Neill |
| D309,710 S | 8/1990 | Groves |
| D310,028 S | 8/1990 | Brandt et al. |
| 4,994,044 A | 2/1991 | Lo Duca |
| 5,078,733 A | 1/1992 | Eveleigh et al. |
| 5,090,583 A | 2/1992 | Hoffman et al. |
| D327,318 S | 6/1992 | Dudar et al. |
| 5,224,937 A | 7/1993 | van der Heiden et al. |
| 5,238,130 A | 8/1993 | Marques et al. |
| 5,275,619 A | 1/1994 | Engebretson et al. |
| 5,405,339 A | 4/1995 | Kohnen et al. |
| 5,451,213 A | 9/1995 | Teicher et al. |
| 5,505,705 A | 4/1996 | Galpin et al. |
| D378,233 S | 2/1997 | Warner |
| 5,624,402 A | 4/1997 | Imbert |
| D395,502 S | 6/1998 | Deily et al. |
| 5,797,885 A | 8/1998 | Rubin |
| D398,060 S | 9/1998 | Brown |
| 5,957,166 A | 9/1999 | Safabash |
| 6,068,614 A | 5/2000 | Kimber et al. |
| D432,916 S | 10/2000 | Drinkwater et al. |
| D435,652 S | 12/2000 | Nazarifar et al. |
| 6,270,519 B1 | 8/2001 | Botts |
| 6,280,418 B1 | 8/2001 | Reinhard et al. |
| D473,647 S | 4/2003 | Francavilla et al. |
| 6,592,251 B2 | 7/2003 | Edwards et al. |
| 6,632,199 B1 | 10/2003 | Tucker et al. |
| 6,726,672 B1 | 4/2004 | Hanly et al. |
| 6,749,092 B2 | 6/2004 | Olechowski et al. |
| 6,821,267 B2 | 11/2004 | Veillon, Jr. et al. |
| D534,796 S | 1/2007 | Falkenburg |
| D547,657 S | 7/2007 | Tacchella |
| 7,316,669 B2 | 1/2008 | Ranalletta |
| 7,503,905 B2 | 3/2009 | Jessop et al. |
| 7,523,967 B2 | 4/2009 | Steppe |
| D596,487 S | 7/2009 | Batton et al. |
| 7,594,681 B2 | 9/2009 | DeCarlo |
| D602,355 S | 10/2009 | Waaland |
| 7,666,170 B2 | 2/2010 | Guala |
| D617,187 S | 6/2010 | Murray |
| 7,740,288 B2 | 6/2010 | Mantell |
| 7,766,919 B2 | 8/2010 | Delmotte |
| 7,799,009 B2 | 9/2010 | Niedospial, Jr. et al. |
| 7,811,278 B2 | 10/2010 | Knipple, Jr. et al. |
| 7,857,284 B2 | 12/2010 | Kimball et al. |
| 7,985,205 B2 | 7/2011 | Adams |
| D644,618 S | 9/2011 | Morihira |
| 8,016,795 B2 | 9/2011 | Barrelle et al. |
| 8,099,932 B2 | 1/2012 | Peacop et al. |
| 8,109,902 B2 | 2/2012 | Middleton et al. |
| 8,152,790 B2 | 4/2012 | Lopez et al. |
| 8,303,571 B2 | 11/2012 | Kraushaar et al. |
| 8,328,768 B2 | 12/2012 | Quigley et al. |
| 8,343,041 B2 | 1/2013 | Byers et al. |
| 8,398,607 B2 | 3/2013 | Fangrow, Jr. |
| D682,688 S | 5/2013 | Murray |
| D684,055 S | 6/2013 | Kwon |
| D684,057 S | 6/2013 | Kwon |
| D686,495 S | 7/2013 | Murray |
| 8,479,370 B2 | 7/2013 | Grant |
| 8,528,757 B2 | 9/2013 | Bisio |
| 8,529,524 B2 | 9/2013 | Newton et al. |
| D691,261 S | 10/2013 | Kawamura |
| D692,143 S | 10/2013 | Shahidi Bonjar |
| 8,551,068 B2 | 10/2013 | Kyle et al. |
| 8,613,738 B2 | 12/2013 | Mantell |
| 8,641,685 B2 | 2/2014 | Mansour et al. |
| 8,679,090 B2 | 3/2014 | Anderson et al. |
| D705,061 S | 5/2014 | Jo et al. |
| D710,695 S | 8/2014 | Pritikin |
| D712,025 S | 8/2014 | Kawamura |
| D712,744 S | 9/2014 | Neputy et al. |
| D713,247 S | 9/2014 | Webster et al. |
| D714,935 S | 10/2014 | Nishioka et al. |
| D715,143 S | 10/2014 | Hewitt et al. |
| D715,146 S | 10/2014 | Holmes |
| 8,852,167 B2 | 10/2014 | Trombley, III et al. |
| 8,870,834 B2 | 10/2014 | Milijasevic |
| D716,636 S | 11/2014 | McDonald |
| D717,948 S | 11/2014 | Strong et al. |
| D726,308 S | 4/2015 | Shubin, Sr. et al. |
| 9,016,473 B2 | 4/2015 | Tamarindo |
| 9,017,295 B2 | 4/2015 | Pan |
| 9,033,938 B2 | 5/2015 | Milijasevic |
| D731,065 S | 6/2015 | Winter |
| D731,647 S | 6/2015 | Nishioka et al. |
| D735,038 S | 7/2015 | Tamarindo |
| 9,073,021 B2 | 7/2015 | Nakamura et al. |
| D736,914 S | 8/2015 | Schultz |
| D736,915 S | 8/2015 | Schultz |
| D737,962 S | 9/2015 | Schultz |
| 9,126,029 B2 | 9/2015 | Fangrow et al. |
| D741,996 S | 10/2015 | Strong et al. |
| 9,149,623 B1 | 10/2015 | Colman |
| 9,289,587 B2 | 3/2016 | Colman |
| D756,200 S | 5/2016 | McDonald |
| D759,486 S | 6/2016 | Ingram et al. |
| 9,427,715 B2 | 8/2016 | Palazzolo et al. |
| 9,433,562 B2 | 9/2016 | Ingram et al. |
| D796,326 S | 9/2017 | Ichikawa et al. |
| 10,001,236 B2 | 6/2018 | Lewis et al. |
| 2004/0116869 A1* | 6/2004 | Heinz ............... A61M 5/347 604/181 |
| 2005/0165351 A1 | 7/2005 | Tamagni, Jr. |
| 2005/0209555 A1 | 9/2005 | Middleton et al. |
| 2006/0217679 A1 | 9/2006 | Hanly et al. |
| 2007/0076401 A1 | 4/2007 | Carrez et al. |
| 2007/0100294 A1* | 5/2007 | Sugita ............... A61M 5/3129 604/241 |
| 2008/0183153 A1 | 7/2008 | Enns |
| 2008/0312640 A1 | 12/2008 | Grant |
| 2009/0230075 A1 | 9/2009 | Springer |
| 2009/0321611 A1 | 12/2009 | Moberg |
| 2010/0022951 A1 | 1/2010 | Ferrera et al. |

(56) References Cited

U.S. PATENT DOCUMENTS

| | | |
|---|---|---|
| 2010/0252564 A1 | 10/2010 | Martinez et al. |
| 2012/0109072 A1* | 5/2012 | Tabata .................. A61M 5/28 604/192 |
| 2014/0020788 A1 | 1/2014 | Kyle et al. |
| 2014/0246616 A1 | 9/2014 | Fangrow |
| 2014/0276466 A1 | 9/2014 | Yeh et al. |
| 2014/0276651 A1 | 9/2014 | Schultz |
| 2014/0323995 A1 | 10/2014 | Clauson et al. |
| 2015/0238747 A1 | 8/2015 | Russo |
| 2016/0001056 A1 | 1/2016 | Nelson et al. |
| 2016/0030293 A1 | 2/2016 | Dorsey et al. |
| 2016/0067147 A1 | 3/2016 | Davis et al. |
| 2016/0067422 A1 | 3/2016 | Davis et al. |
| 2016/0067471 A1 | 3/2016 | Ingram et al. |
| 2016/0143815 A1 | 5/2016 | Koelper et al. |
| 2016/0159635 A1 | 6/2016 | Davis et al. |
| 2016/0206516 A1 | 7/2016 | Kunishige et al. |
| 2016/0206845 A1 | 7/2016 | Colman et al. |
| 2016/0317393 A1 | 11/2016 | Davis et al. |
| 2016/0367439 A1 | 12/2016 | Davis et al. |
| 2017/0014616 A1 | 1/2017 | Davis et al. |
| 2017/0045170 A1 | 2/2017 | Lewis et al. |
| 2017/0239141 A1 | 8/2017 | Davis et al. |

FOREIGN PATENT DOCUMENTS

| | | |
|---|---|---|
| DE | 20302788 U1 | 6/2004 |
| DE | 102005030510 A1 | 1/2007 |
| EP | 0960616 A2 | 12/1999 |
| EP | 2269685 A2 | 1/2011 |
| EP | 3042691 A1 | 7/2016 |
| FR | 2930428 A1 | 10/2009 |
| JP | H10297655 A | 11/1998 |
| JP | 4743229 B2 | 8/2011 |
| WO | 9200717 A1 | 1/1992 |
| WO | 9846278 A1 | 10/1998 |
| WO | 9932155 A2 | 7/1999 |
| WO | 2005065767 A2 | 7/2005 |
| WO | 2008128074 A2 | 10/2008 |
| WO | 2009090627 A1 | 7/2009 |
| WO | 2012024370 A1 | 2/2012 |
| WO | 2013081699 A2 | 6/2013 |
| WO | 2014049097 A1 | 4/2014 |
| WO | 2014160911 A1 | 10/2014 |
| WO | 2015034045 A1 | 3/2015 |
| WO | 2016040126 A1 | 3/2016 |
| WO | 2016089869 A1 | 6/2016 |
| WO | 2018022631 A1 | 2/2018 |

OTHER PUBLICATIONS

Covidien ENFit Coupling; Mar. 2014; 1 pg.
International Search Report & Written Opinion for PCT/US2015/048380; dated Oct. 29, 2015; 10 pgs.
International Search Report & Written Opinion for PCT/US2016/023771; dated Jun. 27, 2016; 17 pgs.
International Search Report & Written Opinion for PCT/US2016/038051; dated Sep. 2, 2016; 13 pgs.
International Search Report & Written Opinion for PCT/US2016/042514; dated Nov. 10, 2016; 12 pgs.
New ISO Tubing Connector Standards: A Follow-Up to the Sentinel Event Alert Webinar PowerPoint Presention; www.jointcommission.org; 50 pgs; Dec. 3, 2014.
New Tube Feeding Connectors Webinar PowerPoint Presention; www.oley.org; 24 pgs; Jun. 24, 2014.
Specialty Medical Products Coupling (Item Code SMP-SCFF); Apr. 10, 2014; 1 pg.
International Search Report & Written Opinion for PCT/US2017/056391; dated Jan. 18, 2018; 16 pgs.
Invitation to Pay Additional Fees for PCT/US2018/021856; dated Jun. 27, 2018; 24 pgs.
International Search Report & Written Opinion for PCT/US2017/019021; dated Sep. 22, 2017; 20 pgs.
Invitation to Pay Additional Fees for PCT/US2017/019021; dated Jun. 6, 2017; 12 pgs.
Baxa (Baxter) Rapidfill Connector, Dec. 1, 2015, 1 pg.
Baxa Self-Righting Luer Tip Caps; www.iso-med.com; Jan. 26, 2017; 1 pg.
Comar Tip Caps; Feb. 10, 2016; 1 pg.
NeoMed Self-Righting Tip Cap; Oct. 7, 2014; 1 pg.
Non Sterile Luer lock to Oral Slip Adapter; Health Care Logistics, Inc.; 1 pg.; Dec. 13, 2016.
Oral Slip to Oral Slip Adapter; Health Care Logistics, Inc.; 1 pg.; Dec. 13, 2016.
Sterile Luer Lock to Oral Slip Adapter; Health Care Logistics, Inc.; 1 pg.; Dec. 13, 2016.
Tulip Medical GEMS Syringe Locks & Single-Use Anaerobic Transfers; 1 pg.; Dec. 13, 2016.
Vygon Fluid Dispensing Connector; 1 pg.; Dec. 13, 2016.

* cited by examiner

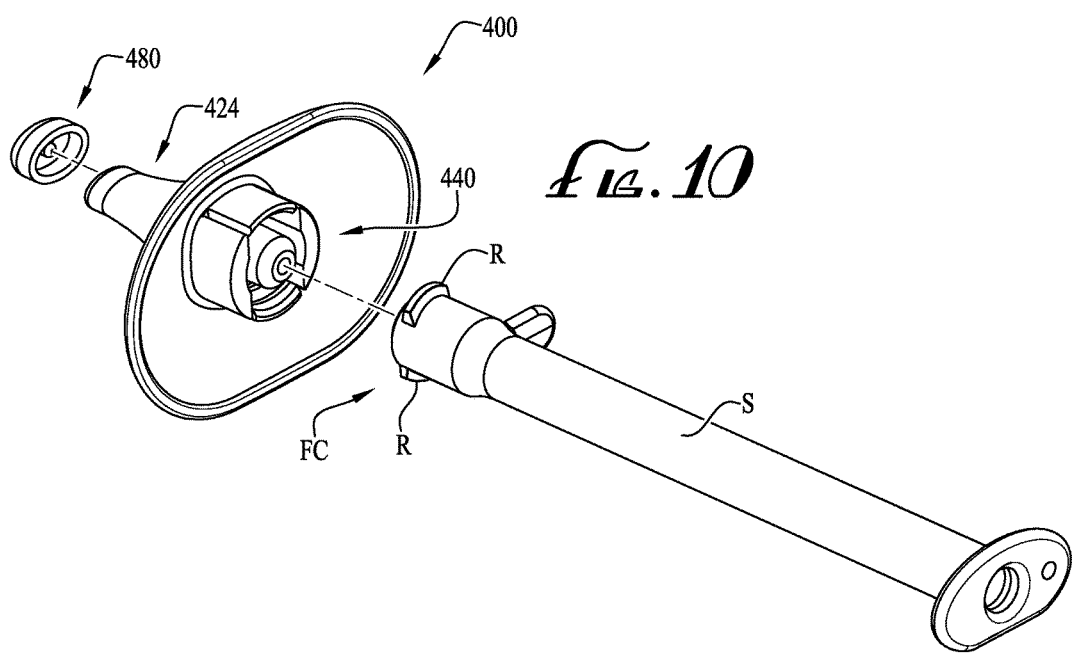
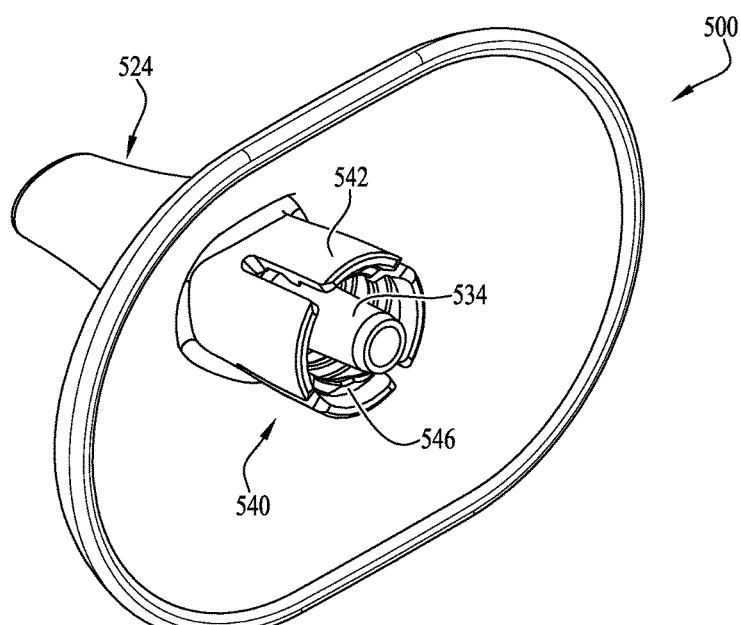

ENTERAL CONNECTORS HAVING COUPLING FEATURES

CROSS-REFERENCE TO RELATED APPLICATIONS

This application is a continuation-in-part of U.S. Non-Provisional application Ser. No. 14/844,922 filed Sep. 3, 2015, which claims the priority benefit of U.S. Provisional Patent Application Ser. No. 62/047,364 filed Sep. 8, 2014, U.S. Provisional Patent Application Ser. No. 62/138,156 filed Mar. 25, 2015, U.S. Provisional Patent Application Ser. No. 62/174,289 filed Jun. 11, 2015, and U.S. Provisional Patent Application Ser. No. 62/192,618 filed Jul. 15, 2015; and is a continuation-in-part of U.S. Non-Provisional application Ser. No. 15/185,583 filed Jun. 17, 2016, which claims the priority benefit of U.S. Provisional Patent Application Ser. No. 62/181,595 filed Jun. 18, 2015; and is a continuation-in-part of U.S. Non-Provisional application Ser. No. 15/078,674 filed Mar. 23, 2016, which claims the priority benefit of U.S. Provisional Patent Application Ser. No. 62/137,293 filed Mar. 24, 2015 and U.S. Provisional Patent Application Ser. No. 62/192,726 filed Jul. 15, 2015.

TECHNICAL FIELD

The present invention relates generally to the field of enteral couplings and connectors, and more particularly to coupling features and mechanisms for use with enteral couplings and connectors.

BACKGROUND

Various fluids such as medications and nutritional fluids are delivered to human or animal patients by dispensing from a syringe. For example, the enteral delivery of formula, breast milk, nutritional supplements, medication and the like to neonatal infants may utilize syringes for manual delivery or automated delivery using a syringe pump. Syringes conforming to the new ENFit design standard (ISO 80369-3) may include a female connector with ribs that is configured for receiving a male coupling surrounded by a fully threaded collar for engagement with the ribs, thereby limiting connection and disconnection between the female connector of the syringe and the male coupling to rotational or twisting movement. Thus, to connect or disconnect one of the male coupling and collar with the female connector and ribs of the syringe, one of the male coupling and collar or female connector and ribs must rotate relative to the other of the male coupling and collar or female connector and ribs. In some example forms, a slip-fit connection can be used between the female connector and the male coupling, however, there's no certainty that the connection is secure.

Thus it can be seen that needs exist for improvements to enteral couplers and the coupling features thereof for coupling with syringes. It is to the provision of enteral couplers having coupling features meeting these and other needs that the present invention is primarily directed.

SUMMARY

In example embodiments, the present invention provides enteral connectors having coupling features for connection with a syringe. In one example embodiment, the syringe includes an ENFit compatible female connector. In another example embodiment, the syringe includes a threaded tip.

In one aspect, the present invention relates to an enteral connector for coupling engagement with a female connector of a syringe. The enteral connector includes a coupling member axially extending along an elongate axis, and a circular array of tabs offset outwardly relative to the elongate axis of the coupling member.

In example embodiments, least one of the tabs includes a thread portion inwardly extending therefrom, and wherein an outer rib of the female connector is configured for removable coupling engagement with the rib portion. In example embodiments, the circular array of tabs includes four tabs, wherein each of the four tabs includes a thread portion formed on an interior surface thereof, and wherein an outer rib of the female connector of the syringe is configured for removable coupling engagement with the rib portions. In example embodiments, with the circular array of four tabs and thread portions formed thereon, the enteral connector is capable of providing a dual-action installation and removal mechanism such that either of a rotational and/or axial movement of one of the enteral connector or the female connector relative to the other of the enteral connector provides for connecting or disconnecting one of the enteral connector or the female connector relative to the other of the enteral connector or the female connector.

In example embodiments, the enteral connector is removably coupled with the female connector by rotational movement of one of the enteral connector or the female connector relative to the other of the enteral connector or the female connector, and wherein the thread portions of the four tabs are generally helical to accommodate a rotational connection and disconnection.

In example embodiments, the enteral connector is removably coupled with the female connector by axial movement of one of the enteral connector or the female connector relative to the other of the enteral connector or the female connector. In example embodiments, axial movement between the female connector and the enteral connector causes the rib to eventually interengage with the thread portions of the tabs, which causes to tabs to generally flex outwardly, thereby permitting the rib to pass by the thread portions.

In example embodiments, the enteral connector is in the form of a tip cap. According to one example embodiment, the coupling member of the tip cap includes an orifice formed therein for accommodating receiving a lumen extension tip of the female connector of the syringe. In example embodiments, the tip cap can be in the form of a self-righting tip cap or can include a flange for acting as a stand. According to one example embodiment, the coupling member of the tip cap includes an orifice formed therein for receiving a lumen extension tip of the female connector of the syringe. According to some example embodiments, the enteral connector can optionally be in the form of an oral administration coupler, a syringe-to-syringe coupler or a fluid transfer lid.

In example embodiments, the circular array of tabs includes a pair of partially flexible tabs oppositely opposed from each other and a pair of generally rigid guide tabs oppositely opposed from each other, and wherein at least one of the partially flexible tabs includes a thread portion formed on an internal portion thereof. In example embodiments, a rib formed on an outer portion of the female connector is configured for engagement with the thread portion of the at least one partially flexible tab when the female connector is connected with the coupling member.

In example embodiments, the enteral connector can be permanently coupled with the female connector by axial movement of one of the enteral connector or the female connector relative to the other of the enteral connector or the female connector, whereby axial coupling engagement of the female connector of the syringe with the coupling member causes the partially flexible tabs to flex outwardly to a flexed state, permitting the rib to pass by the thread portion, and returning to a neutral state whereby the rib of the female connector is engaged with the rib portion and preventing disconnection between the female connector and the enteral connector. In example embodiments, the guide tabs prevent rotation of the female connector relative to the coupling member by interference between the guide tabs and ribs formed on an outer surface portion of the female connector.

In example embodiments, the female connector of the syringe includes an ENFit compatible female connector. Optionally, the female connector of the syringe includes a threaded tip.

In another aspect, the present invention relates to coupling features for an enteral connector. The enteral connector includes an ENFit compatible coupling member. The coupling features include a circular array of clips formed around the ENFit compatible coupling member, and a thread portion formed on an interior portion of at least one of the clips.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 10 is a perspective assembly view of the oral administration coupler of FIG. 7 positioned between a syringe and a capping member.

FIG. 11 is a perspective view of an oral administration coupler according to another example embodiment of the present invention.

DETAILED DESCRIPTION OF EXAMPLE EMBODIMENTS

Figure 1:
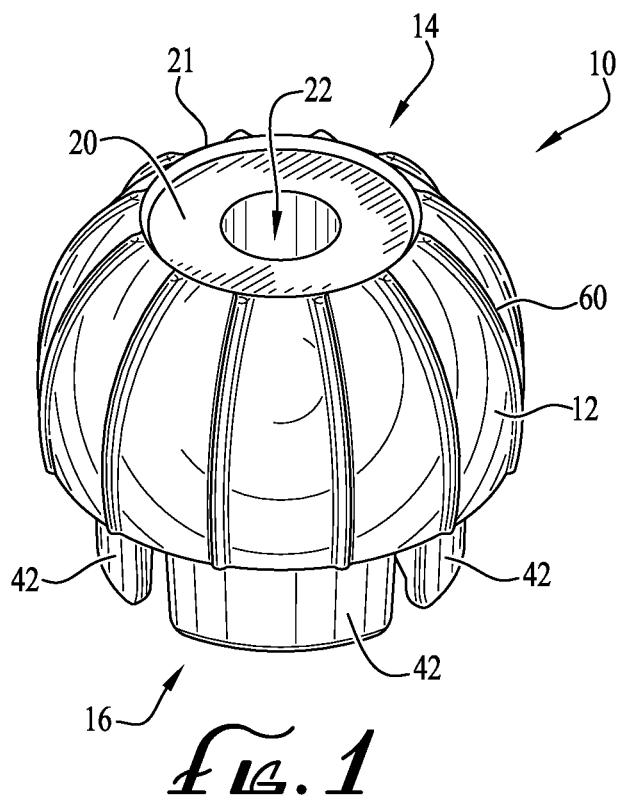
FIG. 1 is a perspective view of a tip cap according to an example embodiment of the present invention, and showing the tip cap comprising a plurality of clips for providing removable engagement with a syringe coupling.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-26 show a plurality of enteral connectors and couplers comprising various coupling features according to example embodiments of the present invention. As will be described herein, the enteral connectors may take various forms, for example, tip caps, oral administration couplers, syringe-to-syringe couplers, end capping members, fluid transfer connectors, syringe couplings, etc.

Figure 2:
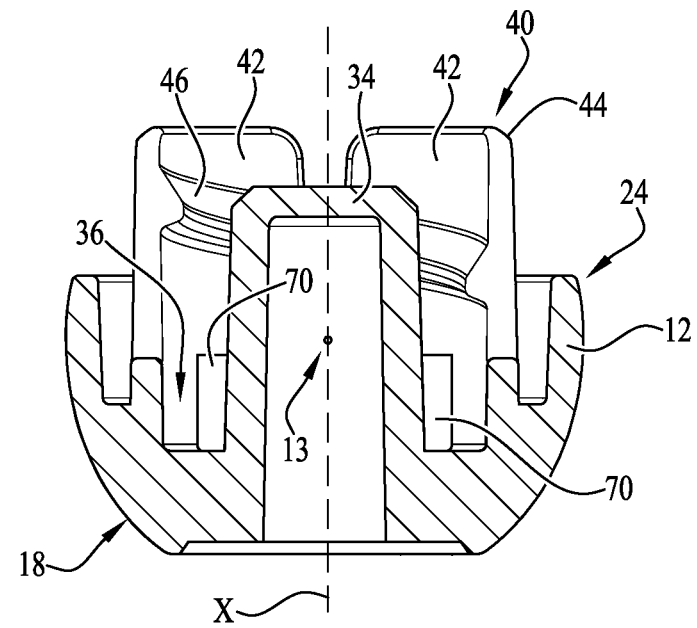
FIG. 2 is a cross-sectional view of the tip cap of FIG. 1.

FIGS. 1-2 show a tip cap 10 according to an example embodiment of the present invention. In example forms, the tip cap 10 generally comprises a bulbous shell or body 12 having a first end 14 and a second end 16. The cap body 12 generally comprises an oblate spheroid external geometry that is somewhat flattened at the ends 14, 16 of its minor axis or elongate axis X, although other shell geometries may be utilized. Preferably, the body 12 is formed such that the tip cap 10 will tend to right itself and come to equilibrium in a particular orientation (i.e., coupling side (second end 16 up) when coming into contact with a support surface under the influence of gravity, at least in a majority of instances and preferably in a substantial majority or substantially all instances. The first end 14 comprises a generally planar rim or generally conical raised edge 21 around a base surface 20 that generally surrounds an orifice 22, and the second end 16 comprises a split collar or circular array of couplings 40, which generally extend from the cap body 12. In example forms, a rim 24 is provided near an end of the body 12 near the second end 16. Typically, the rim 24 is substantially radiused to further assist the cap 10 in righting itself so that the planar rim or generally conical raised edge 21 is resting against a support surface.

According to some example embodiments, the rim 24 generally provides a smooth transition between the outer surface of the body 12 and the edge of the extension thereof extending towards the second end 16. According to some example embodiments, the base surface 20 is recessed within the body 12 whereby the planar rim or generally conical raised edge 21 becomes in contact with the surface such that the tip cap 10 is positioned in a coupling-side-up orientation, for example, whereby the coupling 34 is generally extending in a direction generally opposite the surface and whereby the base surface 20 is generally laterally offset from the surface. Optionally, the raised edge 21 can be shaped as desired, for example with a chamfered edge or other radiused edges or other transitional features as desired. According to some example forms, one or more cutouts may be formed in portions of the edge 21 for example, such that the area of the contact surface of the edge 21 in contact with the surface is reduced. Optionally, one or more additional ring-like intents may be formed on the base surface 20 (and around the orifice to increase the surface area in contact with the surface).

In example forms, four tab members or clips 42 generally form the circular array of couplings 40 at a distance from the coupling 34 generally extending centrally from the body 12, which generally forms a portion of the orifice 22. Typically, each clip 42 comprises a chamfered, angled or radiused end portion 44 near an outer edge thereof, and an internal portion or wall of at least one of the clips 42 preferably comprises a thread or thread-like ridge 46 generally protruding therefrom. In the depicted embodiment, each of the four clips 42 comprises at least a portion of a thread 46. Optionally, some of the clips 42 do not have a thread 46 on the internal portion or wall, for example, to reduce frictional engagement with the threaded portion such that the installation thereon and removability from the syringe coupling can be adjusted as desired (e.g., the force required to install or sealingly engage tip cap with syringe coupling and the force required to remove the sealingly engaged tip cap (either by axial or rotational movement of tip cap relative to syringe connector) can be adjusted as desired). In example forms, the tip cap 10 can be installed and removed (to/from the syringe) either by pushing and pulling (without twisting) due to the snap connection provided by the split collar 40, or by twisting on and off due to the thread 46 on the clips 42, thus providing a dual-action installation and removal mechanism. In example embodiments, the array of coupling can provide for a two-way coupling action, for example, whereby either rotation and/or axial movement between the coupling and the syringe connector provide for removably connecting the tip cap with the syringe connector.

Preferably, with the edge 21 resting against a generally flat support surface, a female connector FC of a syringe S (see FIGS. 4 and 10) can be pressed against the second end 16 thereof to provide interengagement therebetween. Preferably, the ribs R eventually interengage with the threads 46 of the clips 42, which causes the clips 42 to generally flex outwardly to a flexed state, thereby permitting the ribs R to pass by the threads 46. Preferably, the clips 42 are substantially resilient and flexible such that interengagement of the ribs R with the threads 46 allows for outward flexure of the clips 42, but the clips 42 generally return to a neutral, unflexed state after the passing of the ribs R. In example embodiments, when the female connector FC is at least partially seated within an annular recess 36 defined between the coupling 34 and the clips 42, the ribs R become at least partially engaged with at least a portion of one of the threads 46 of the clips 42, and thus, the tip cap 10 is prevented from being easily pulled away from the female connector FC. However, the tip cap 10 can be removed from the female connector FC by rotation thereof relative to the female connector FC whereby the ribs R are guided along the threads 46, for example, similar to the rotational threading engagement of a nut and bolt. In some example embodiments, inserting the female connector FC within the cap 10 preferably causes the rotation of the cap 10 as the female connector FC is inserted therein, for example, wherein the ribs R of the female connector FC move along the threads 46 and wherein the clips 42 are substantially rigid such that interengagement of the ribs R with the threads 46 provides rotation thereto rather than outwardly flexure of the clips 42. In most example forms, the clips 42 and/or threads 46 of the cap comprise a lead-in or angle or taper, which allows for a friction/interference fit. In some example embodiments, the coupling 34 is configured to provide a friction/interference fit with the female connector FC when the tip cap 10 is coupled to the female connector FC of the syringe S. U.S. Published Patent Application 2016/0067422 discloses a tip cap having one or more clips for providing a dual-action installation and removal mechanism, which is incorporated by reference herein for all purposes.

In example embodiments, at least one tactile rib or support 70 is formed within an annular recess 36, which generally extends between the coupling 34 and an inner radial wall of the clips 42. In example forms, the tip cap 10 comprises four equally spaced supports 70 positioned about the annular recess. Generally, the supports 70 define four sections within the annular recess 36 whereby each of the supports 70 are generally centrally-positioned between their respective clip 42. According to some preferred forms, the supports 70 provide an amount of rigidity to the clips 42 such that they are generally flexible yet comprise a greater rigidity than clips without supports. In example forms, the curved outer surface 18 can comprise a radial array of rib-like indentions or nubs 60 extending along the curved outer surface 18 of the body 12. In example forms, the nubs 60 preferably assist in a user gripping and/or twisting the tip cap 10, for example, for removing the tip cap 10 from engagement with the female connector FC of the syringe S.

Figure 3:
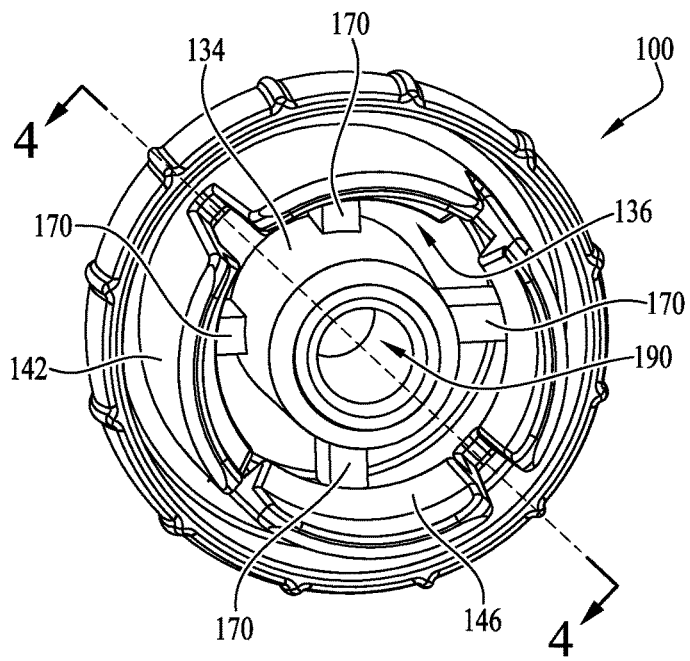
FIG. 3 is a perspective end view of a tip cap according to another example embodiment of the present invention.
Figure 4:
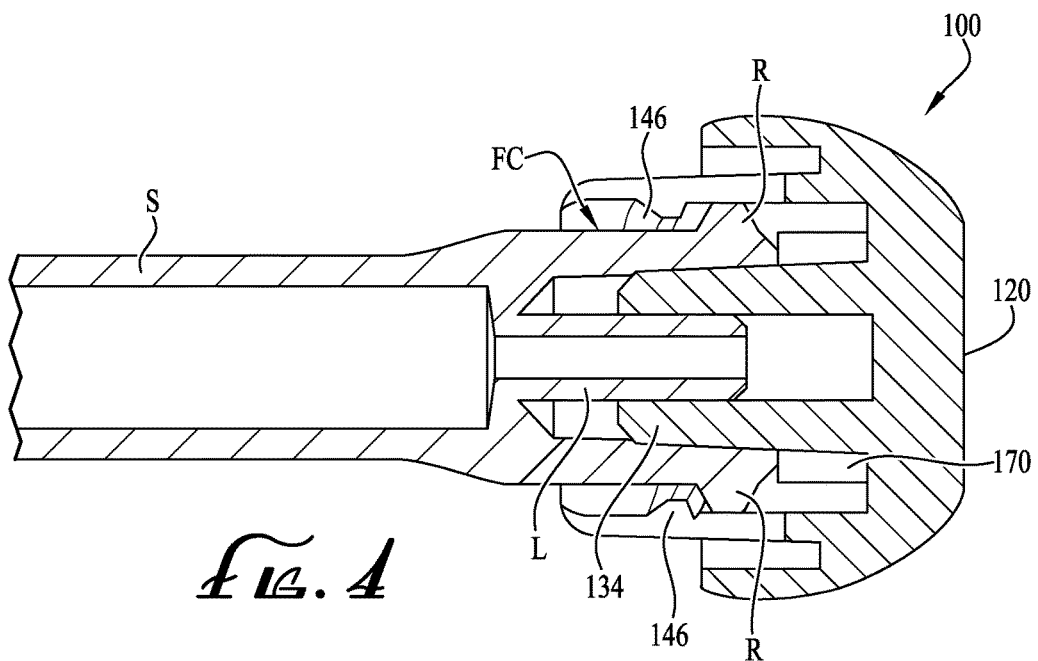
FIG. 4 is a cross-sectional view of the tip cap of FIG. 3 removably mounted to a syringe tip according to an example embodiment of the present invention.

FIGS. 3-4 show a tip cap 100 according to another example embodiment of the present invention. As depicted, the tip cap 100 is generally similar to the tip cap 10 as described above. In example forms, the coupling 134 comprises an orifice 190 formed therein, for example, which accommodates receiving a lumen extension tip L provided on the female connector FC of the syringe (see FIG. 4). Optionally, one or more openings can be formed and extend through portions of the tip caps 10, 100, for example, from an outer portion of the base surface 20, 120 to within at least a portion of the annular recess 36, 136. In example forms, the one or more openings preferably mitigate potential choking hazards, and/or to provide drainage and venting of any fluid accumulation within the tip cap. As similarly described above with respect to the tip cap 10, four tab members or clips 142 generally form the circular array of couplings, which are spaced outwardly at a distance away from the coupling 134. In the same manner, the clips 142 preferably provide for a dual-action installation and removal mechanism.

Figure 5:
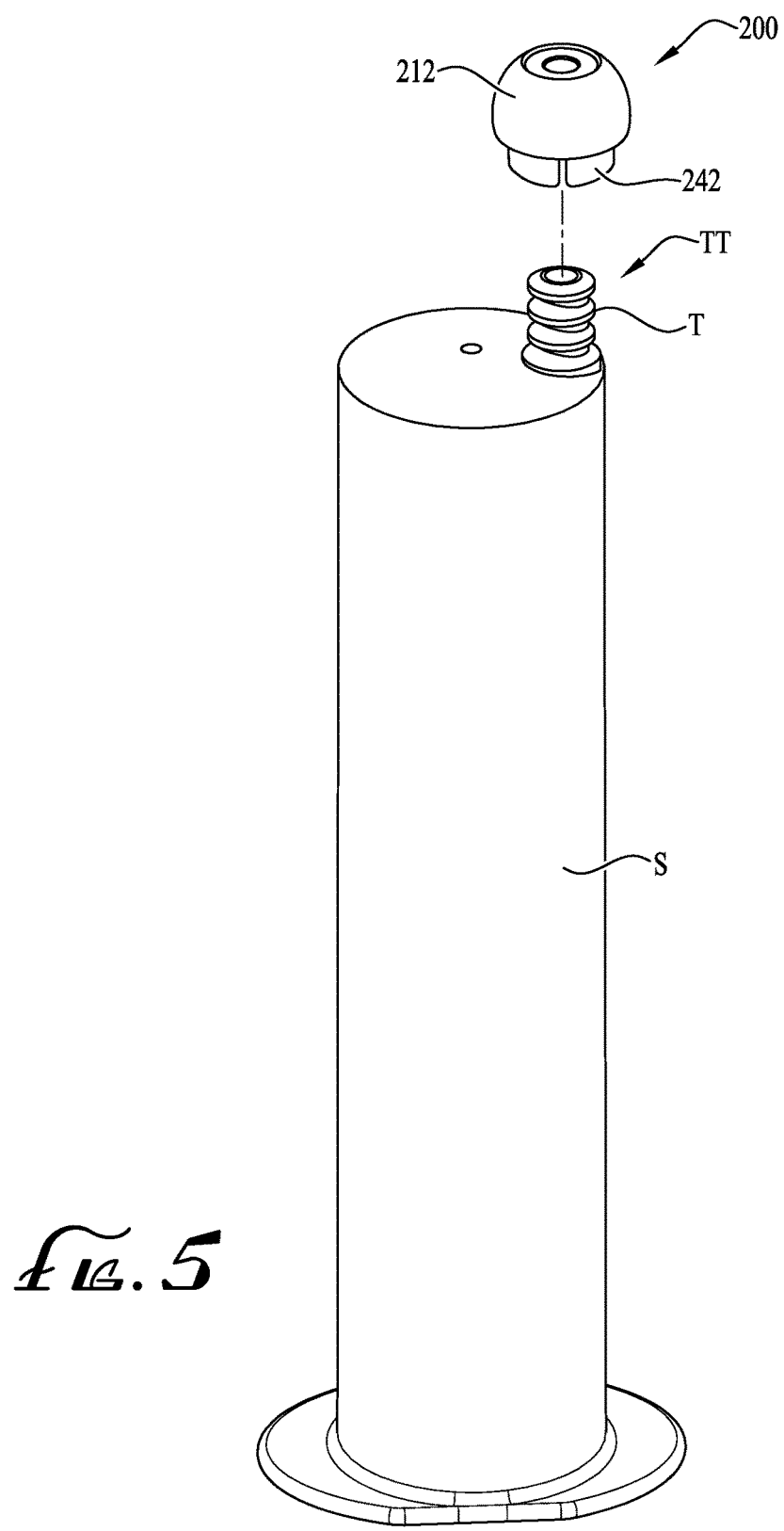
FIG. 5 is a perspective view of a tip cap and a syringe comprising a fully threaded tip for receiving the tip cap according to another example embodiment of the present invention.

As depicted in FIG. 5, a tip cap 200, which is generally similar to the tip caps 10, 100 as depicted above, can be configured for removable engagement with a threaded tip TT, for example, rather than an EN Fit compatible female connector FC. Thus, in a similar manner, the tip cap 200 comprises a circular array of clips 242 thereon that are configured for removable engagement with the threads T of the threaded tip TT. In example embodiments, the threaded tip TT comprises helical threads T extending along the entirety thereof, and the clips 242 preferably provide for removable engagement with the threaded tip TT, for example, wherein at least one of the clips 242 comprises a thread formed on an internal portion thereof, whereby engagement of the clips 242 with the threads T of the threaded tip TT cause outwardly flexure of the clips 242, wherein engagement of the threads of the one or more clips 242 engages the thread T of the threaded tip TT, thereby causing the one or more clips 242 to flex and become seated within a portion of a channel defined by the helically spaced apart threads T. U.S. Published Patent Application 2016/0067422 discloses further details of a tip cap for removable engagement with a threaded tip TT, and further details and dimensions of the threaded tip TT, which are incorporated by reference herein for all purposes. As similarly described above, the clips 242 preferably provide for a dual-action installation and removal mechanism.

Figure 6:
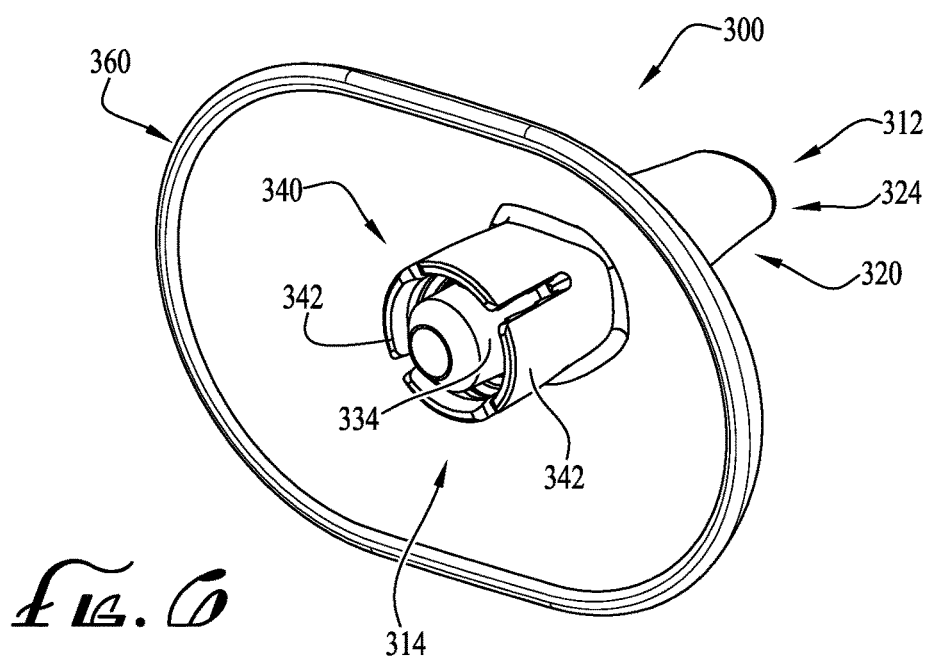
FIG. 6 is a perspective view of an oral administration coupler according to an example embodiment of the present invention, the oral administration coupler comprising a coupling portion having a plurality of releasably engageable clips.
Figure 7:
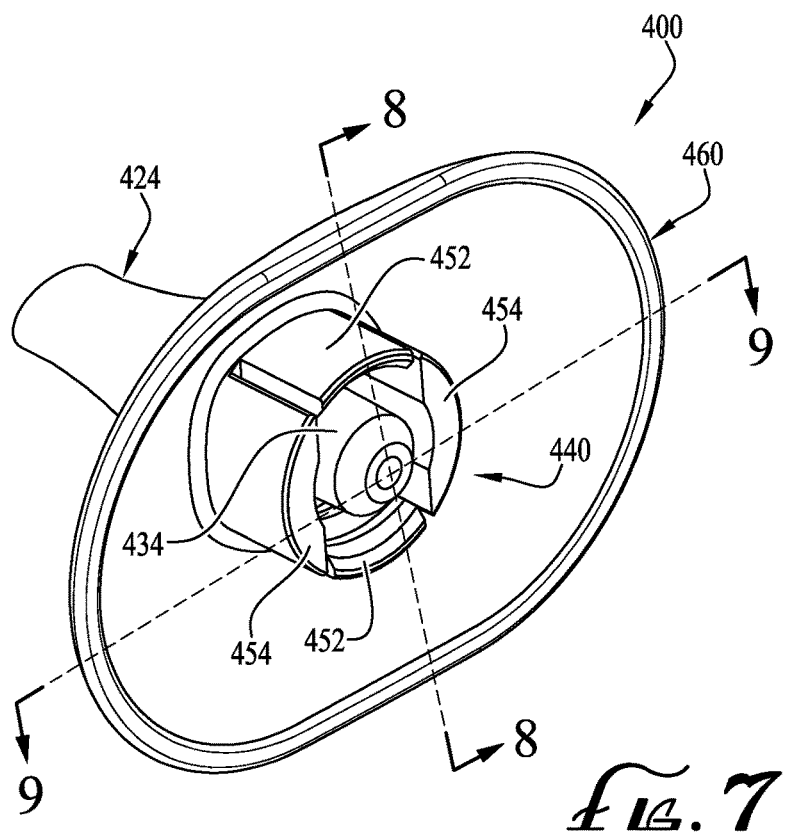
FIG. 7 is a perspective view of an oral administration coupler according to another example embodiment of the present invention.

FIGS. 6-11 show a plurality of oral administration couplers according to additional example embodiments of the present invention. As depicted in FIG. 6, the oral administration coupler generally comprises a central fluid transfer member 320 extending from a first end 312 to a second end 314, and an outer flange 360 is generally positioned between the first and second ends 312, 314 of the central fluid transfer member and extending outwardly therefrom. The central fluid transfer member 320 generally comprises an elongate stem or oral delivery applicator 324 at the first end 312 of the fluid transfer member 320 and an ENFit compatible coupling or connector 334 positioned at the second end 314 of the fluid transfer member 320. In example forms, the oral delivery applicator 324 generally extends in a direction that is substantially opposite to the direction of the extension of the connector 334. The flange 360 is generally integrally formed with the fluid transfer member 320 between the first and second ends 312, 314 of the fluid transfer member 20.

As is similarly described above, a collar 340 comprises radial clips 342 surrounding the coupling 334 to provide a dual action installation and removal mechanism for removable engagement with the female connector FC of the syringe S. As shown in FIG. 6, the collar 340 comprises a substantially uniform circular array of clips 342 are formed around the coupling 334, which provide for a push-on or snap-fit coupling engagement with the female connector FC of the syringe S. In example embodiments, a portion of a thread is formed on an internal portion of each clip 342 for providing engagement with the ribs R of the female connector FC of the syringe S. For example, according to some example embodiments, the thread portion formed on each of the clips 342 generally extends along a helical path, for example, to provide for complementary interengagement with the ribs R of the female connector FC during a rotational installation or removal of the oral administration coupler 300 to/from the female connector FC. Optionally, instead of screwing or rotating one of the oral administration coupler 300 or female connector FC relative to the other to provide engagement therebetween, the female connector FC can optionally be generally axially advanced relative to the coupling 334 so that the coupler 300 becomes removably engaged with the syringe S. In example forms, the flexible fingers or clips 342 generally flex outwardly such that the female connector FC can become engaged with the collar 340, for example, thereby causing the ribs R to become engaged with the thread portions of each clip 342. In example forms, the female connector FC and the ribs R thereof being generally axially advanced relative to the clips 342 causes the ribs R to become engaged with the thread portions of the clips 342, and wherein further axial advancement of the female connector FC enables the ribs R to cause outward flexure of the clips 342, and then back to a neutral state, for example, wherein the ribs are generally removably engaged with the thread portions of the clips 342. In example forms, to remove the coupler 300 from the female connector FC of the syringe S, one of the coupler 300 or the female connector FC is generally rotated relative to the other of the coupler 300 or female connector FC. Optionally, the flexibility of the clips 342 and the extension of the thread portions inwardly from an internal portion of the clips 342 towards the coupling 335 can be adjusted to reduce or increase the axial force required for installation and/or removal.

Figure 8:
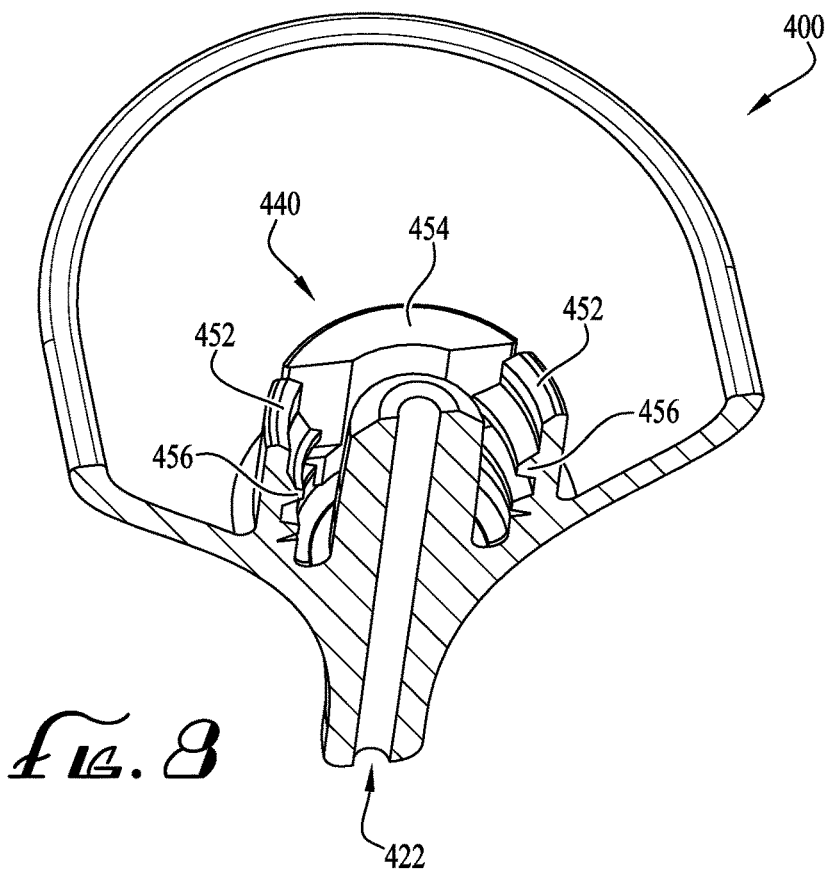
FIG. 8 is a perspective cross-sectional view of the oral administration coupler of FIG. 7 taken along line 8-8.
Figure 9:
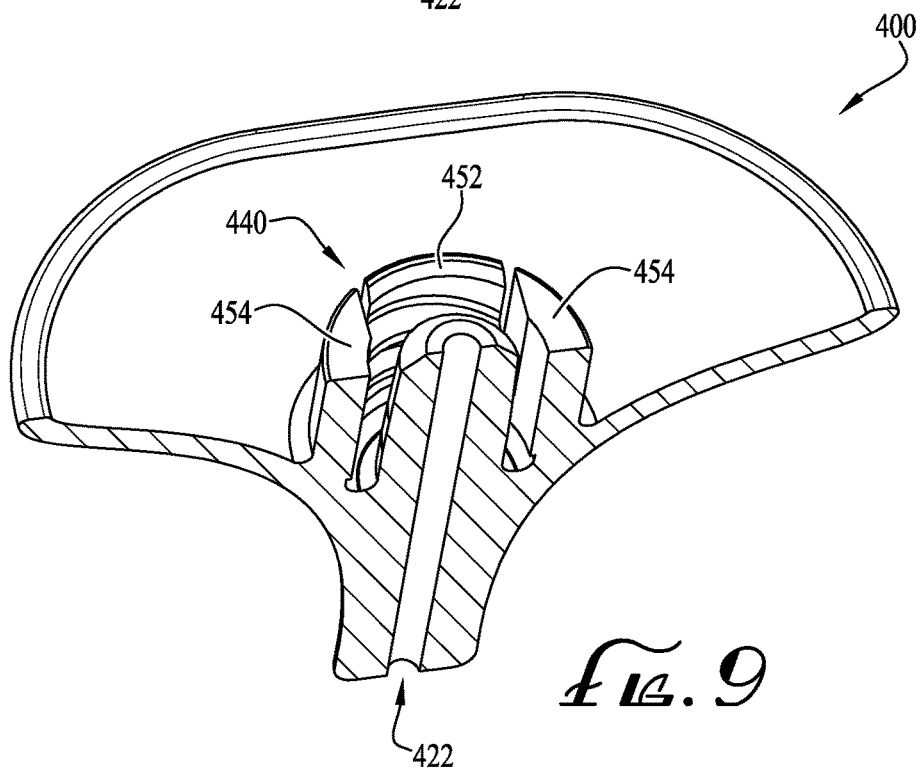
FIG. 9 is a perspective cross-sectional view of the oral administration coupler of FIG. 7 taken along line 9-9.

FIGS. 7-10 show an oral administration coupler 400 according to another example embodiment of the present invention. In example embodiments, the oral administration coupler 400 comprises a modified ENFit compatible coupling 440. As depicted, the coupling 440 comprises a locking hub connection whereby the female connector FC is substantially permanently connected once coupled there-with. For example, the coupling 440 generally surrounds the coupling 434 and comprises a pair of clips 452 extending outwardly on opposite sides of each other, and the sides generally adjacent the clips comprise substantially rigid supports or guide tabs 454. As shown in FIG. 8, the clips generally comprise at least one or more ribs or threads 456 on an internal portion thereof, which preferably provide for interengagement with the ribs R of the female connector FC. However, as shown in FIG. 9, the guide tabs 454 do not comprise any threads and are substantially thicker than the clips 452. Thus, during engagement of the female connector FC with the coupler 400, the ribs R are generally oriented to interengage with the threads 456 of the clips 452. Preferably, as similarly described above, the clips 452 are at least partially flexible such that the ribs R of the female connector FC pass by the threads of the clips when the clips are forced to flex outwardly. Once the coupling is coupled to the female connector FC, the coupling is prevented from rotating due to the guide tabs interfering with the ribs R of the female connector FC. Furthermore, the clips are at least partially rigid such that the female connector is generally prevented from being pulled apart from the female connector FC.

Optionally, as depicted in FIG. 10, the distal end of the coupling may be provided with a cap or closure 480. In example forms, the closure 480 is generally shaped similarly to the distal end of the coupling and comprises a nipple therein for extending within the lumen of the coupling. Preferably, the closure 480 may be shaped and sized as desired. Typically, the closure 480 will generally be shaped and sized to provide a generally tight yet removable fit with the distal end of the coupling, for example, which may be in the form a friction fit connection, a twist-on and/or snap-on, or other connections as desired. According to some example forms, the closure 480 may be permanently coupled with the distal end of the coupling once coupled thereto. In some example forms, the closure 480 is tethered with the coupling but without interfering with the administration of fluids from the distal end thereof. As depicted, the closure 480 is a separate piece. Preferably, the closure prevents fluids that may be within the lumen of the coupling from exiting therefrom.

Optionally, according to additional example embodiments of the present invention, the oral administration coupler can be in the form of a connection hub (e.g., with the clips extending therefrom) and a generally flexible tubing member, for example, which can be configured for back-of-mouth delivery such that the output of fluids from the coupler, syringe or other accessory is such that the tongue of the patient receiving the fluids is bypassed. U.S. Provisional Patent Application No. 62/396,532 discloses further details of oral administration coupler configured for back-of-mouth delivery, the entirety of which is incorporated by reference herein for all purposes. In example embodiments, the connection hub is a modified ENFit compatible coupling, for example, wherein one or more flexible clips (as similarly described above) are formed around the coupling for providing engagement with the ribs of a female connector. According to example embodiments, the connection hub can be configured for permanent or removable engagement with the ribs of the female connector. According to one example embodiment, the connection hub is preferably configured similarly to the locking hub coupling 440 of the oral administration coupler 400, for example, to provide for a permanent connection with the female connector (and ribs thereof). Optionally, the connection hub can be configured for removable engagement with a threaded tip TT.

FIG. 11 shows an oral administration coupler 500 according to another example embodiment of the present invention. As depicted, the coupler 500 is substantially similar to the coupler 300 as described above. In example embodiments, the coupling 540 comprises four clips 542 arranged in a circular array around the coupling 534, which comprise threads 546 formed thereon for providing removable engagement with a threaded tip TT (see FIG. 5).

Figure 12:
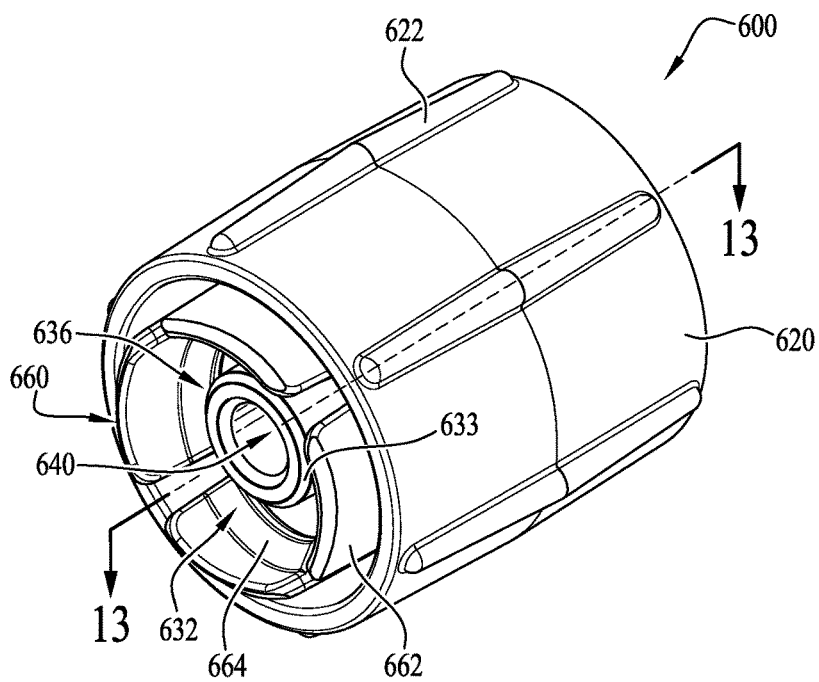
FIG. 12 is a perspective view of a syringe-to-syringe coupler according to an example embodiment of the present invention.
Figure 13:
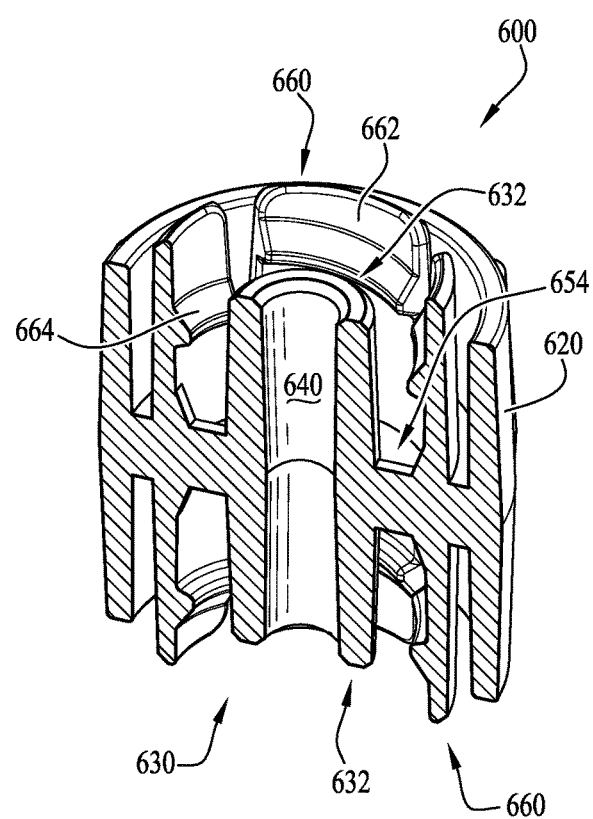
FIG. 13 is a perspective cross-sectional view of the syringe-to-syringe coupler of FIG. 12 taken along line 13-13.
Figure 14:
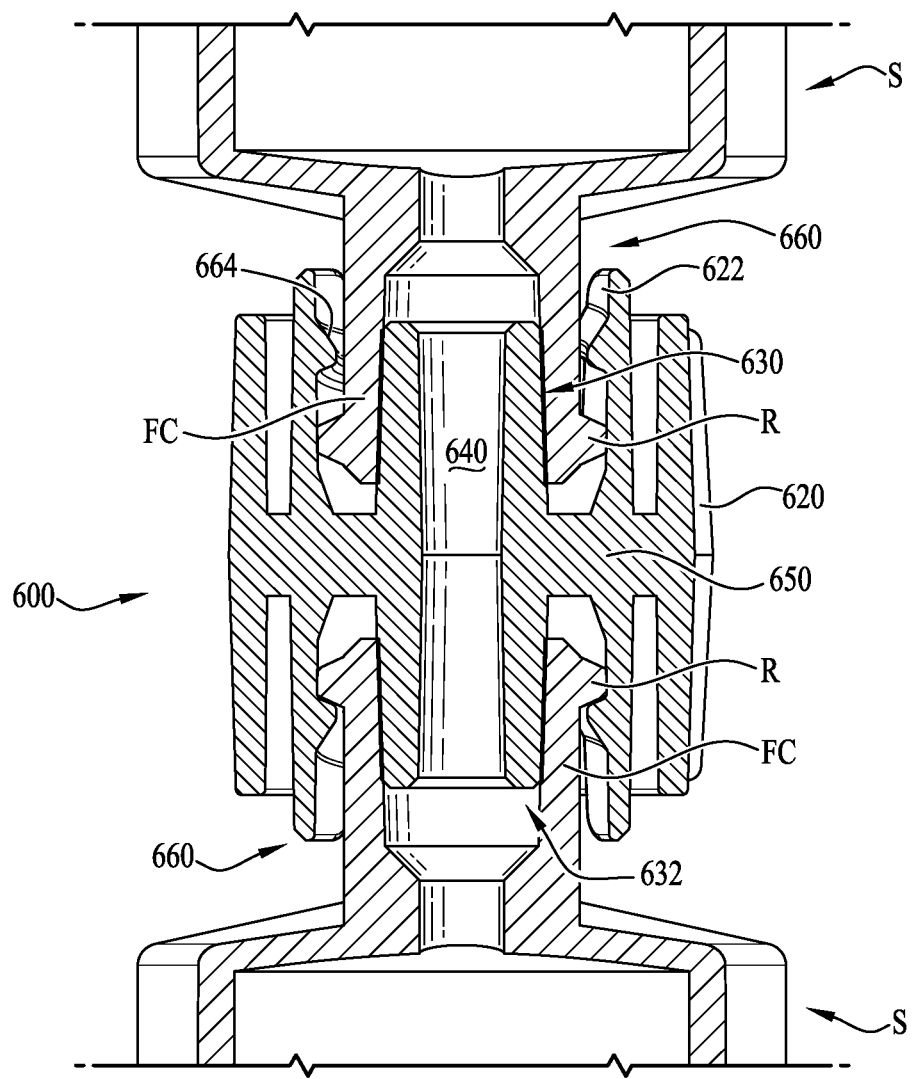
FIG. 14 is the cross-sectional view of the syringe-to-syringe coupler of FIG. 12, and showing a syringe coupling mounted to each end of the syringe-to-syringe coupler.

FIGS. 12-21 show a plurality of syringe-to-syringe couplers according to example embodiments of the present invention. FIGS. 12-14 show a syringe-to-syringe coupler 600 according to one example embodiment of the present invention. In example embodiments, the coupler 600 is configured to removably couple two syringes S together to facilitate the transfer of fluids therebetween. In example embodiments, the coupler 600 includes a hub 630 and fluid conduit 640 of similar size and shape as the previously described embodiment. The coupler 600 includes engagement members or coupling elements 660 (forming a split collar) provided at each end of the coupler 600 and generally surrounding the hub 630. In example embodiments, each coupling element 660 comprises four tab members or clips 662 that generally form a circular array at a distance from the hub 630 generally extending from a central portion or midpoint of the hub 630 toward one of the male tips 632. An internal portion or wall of at least one of the clips 662 includes a threaded portion 664. In the depicted embodiment, each of the four clips 662 includes at least a portion of a thread 664. In example forms, the female connector FC of each syringe S can be installed and removed by either pushing and pulling (without twisting) due to the snap connection provided by the split collar and the rib R, or by twisting on and off due to the thread 664 on the clips 662, thus providing a dual-action installation and removal mechanism. In the depicted embodiment, the hub 630 and coupling elements 660 are coaxially positioned within a cylindrically shaped outer body 620. In example embodiments, at least one connecting member or transverse flange 650 is provided for retaining the hub 630 concentrically or coaxially within the outer cylindrical housing 620 of the coupling 600. As such, one or more vents 654 can be provided as desired.

In alternative example forms, the female connector FC of each syringe S can be installed with the coupling 600 by pushing (without twisting) due to the snap connection provided by the split collar and the rib R (e.g., flexibility of the clips 662), but is generally prevented from being pulled therefrom, for example, unless the syringe S or coupling 600 is generally rotated relative to the other. Optionally, attachment can be provided by twisting on and off due to the thread 664 on the clips 662, for example, whereby engagement of the rib R of the female connector FC with the threads 664 provide axial movement therebetween for attachment or detachment from the female connector FC. Preferably, in some example embodiments, the allowable flexibility of the clips 662 can be adjusted such that attachment and detachment (pushing, pulling, twisting) of the syringe S and coupling 600 can be configured as desired.

According to one example form, the clips 662 preferably provide the user with tactile feedback during attachment (and/or detachment) of the coupling 600 to/from the syringe S. For example, according to some example forms, the flexibility of the clips during interengagement with the female connector FC of the syringe S causes the clips to snap back into place, for example, after being flexed outwardly due to engagement with the ribs R of the female connector FC. Thus, according to example forms of the invention, the coupling 600 can preferably provide the user with an indication that the coupling is generally securely coupled with the female connector FC. Optionally, after the clips provide the tactile feedback (e.g., indicating engagement therebetween), the user may further twist the coupling 600 relative to the female connector FC to ensure the connection therebetween is substantially snug and secure.

Figure 15:
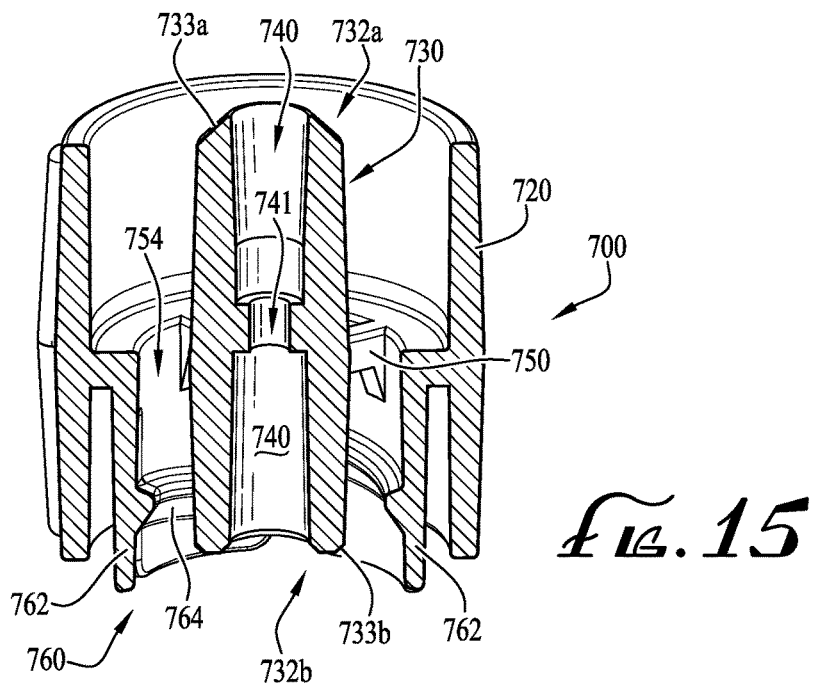
FIG. 15 is a cross-sectional view of a syringe-to-syringe coupler according to another example embodiment of the present invention.

FIG. 15 shows a syringe-to-syringe coupler 700 according to another example embodiment of the present invention. The coupler 700 is configured to removably engage a first syringe S with a slip-fit coupling and a second syringe with a threaded coupling. In example embodiments, the coupler 700 includes a hub 730, fluid conduit 740 and outer body 720 of similar size and shape as the previously described embodiment. In example embodiments, a neck or ring is provided within the conduit 740, which can further reduce the volume of the conduit, for example, by providing a generally smaller intermediate conduit portion 741, which is generally positioned ata midpoint of the conduit 740. In example embodiments, one of the ends of the hub comprises a first male tip 732*a* (e.g., configured for a slip-fit connection) and the other end of the hub 730 comprises a second male tip 732*b* (e.g., similar to the male tips 632 of coupling 600). In example embodiments, the first male tip 732*a* comprises a chamfered edge 733*a* formed at an end portion of the tip 732*a* and the second male tip 732*b* comprises a radiused edge 733*b* formed an end portion of the tip 732*b*. In example embodiments, due to the first male tip 732*a* being configured for a slip-fit connection, the chamfered edge 733*a* preferably facilitates the frictional engagement with an internal portion of the female connector FC.

Figure 16:
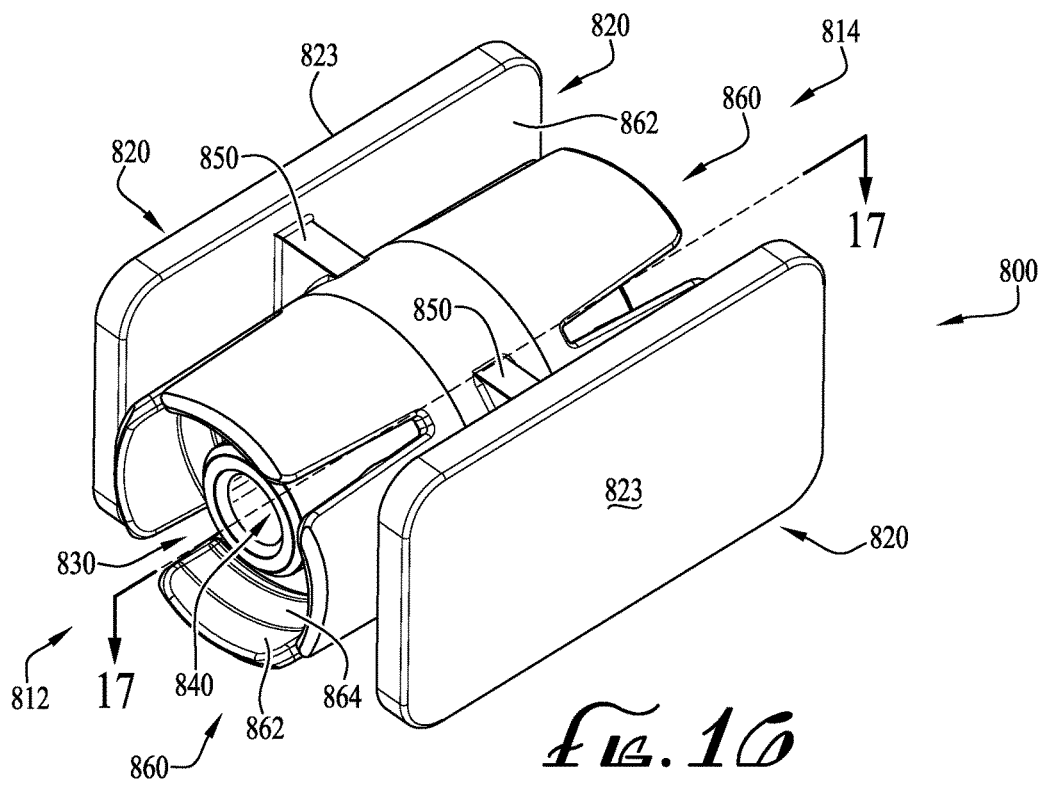
FIG. 16 is a perspective view of a syringe-to-syringe coupler according to another example embodiment of the present invention.
Figure 17:
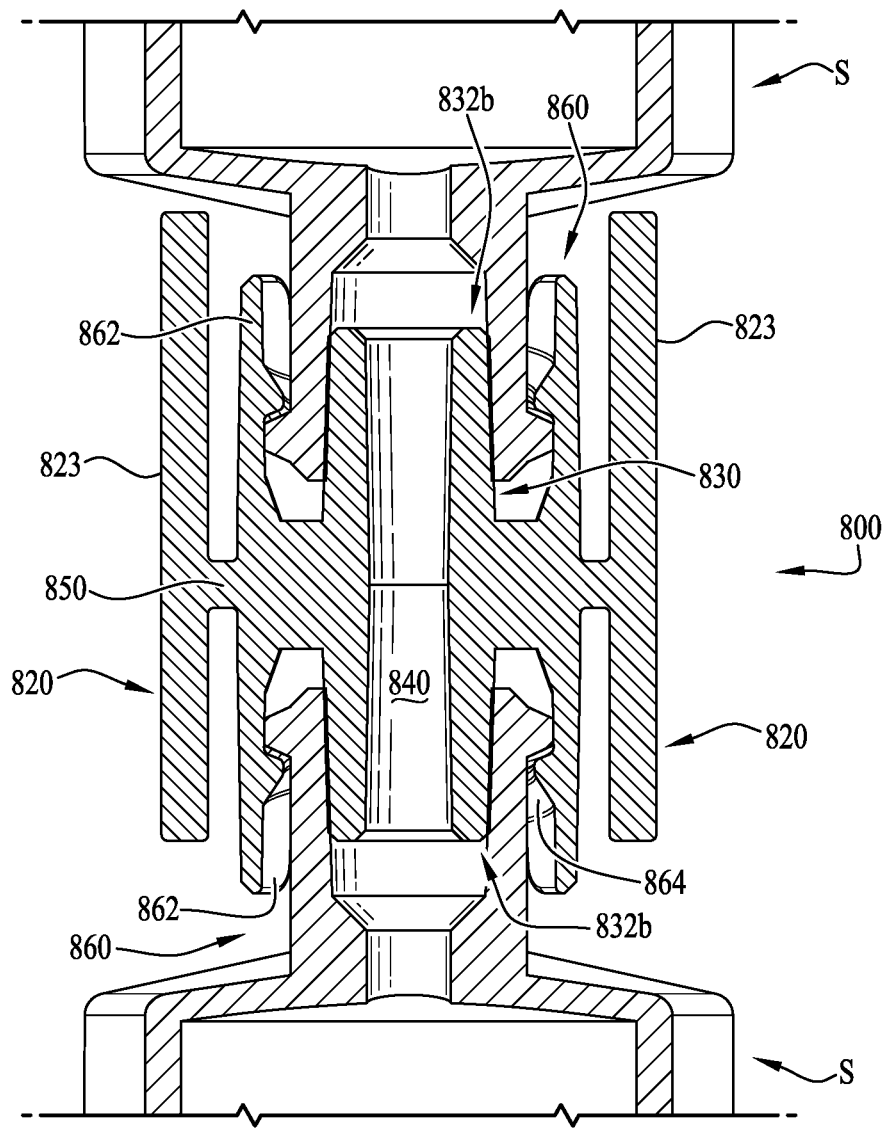
FIG. 17 is a cross-sectional view of the syringe-to-syringe coupler of FIG. 16, and showing a syringe coupling removably mounted to each end of the syringe-to-syringe coupler.

FIGS. 16-17 show a syringe-to-syringe coupler 800 according to another example embodiment of the present invention. The coupler 800 is configured to removably engage two syringes S with threaded couplings, or for example, a female connector FC comprising a pair of ribs. The coupler includes a hub 830 and fluid conduit 840 of similar size and shape as the coupler 600. The coupler 800 also includes two coupling elements 860 comprising four clips 862 with threaded portions 864 similar to previously described coupler 600. In the depicted embodiment, the coupler 800 further includes two generally oppositely-positioned and outwardly offset planar members or gripping panels 820 attached to the outer surface of the coupling elements 860. The panels 820 are oriented on opposite sides of the cylindrical coupling elements such that the inner face of the panel 822 is oriented toward the length of the hub 830, for example such that the elongate extension of each of the panels 820 is generally oriented parallel with the extension of the hub 830. In example embodiments, an exterior or outer surface 823 of one or both of the panels 820 can comprise one or more openings, indentations, recesses, protrusions or other texturizing or grip-enhancing surface features to provide a gripping surface for a user that is grasping the coupling 800, for example, by placement of one or more fingers against the outer surface 823 generally providing a squeezing-like action with two or more fingers.

In the depicted example embodiment, the panels are offset with respect to the length or extension of the hub 830, for example, such that the length of the panel 820 is not centered with the length of the hub 830, and thus causing one of the coupling elements 860 to extend beyond the end of the ends of the panels 820, for example, at a first end 812 of the coupler 800, and wherein another of the coupling elements 860 is generally positioned to be at least partially recessed below the ends of the panels 820 as is shown at the second end 814.

In alternate example embodiments, the panels 820 can be positioned and oriented as desired with respect to the hub 830. Accordingly, according to example embodiments, the coupling 800 is generally similar to the coupling 600 as described above, for example, wherein the hubs 630, 830, the fluid conduits 640, 840, and the transverse flanges 650, 850 are substantially similar in size and functionality, and wherein the cylindrical outer body 620 is generally replaced with the oppositely-positioned and outwardly offset planar members 820 to define the coupling 800. According to some example forms, one or more openings (or openings extending entirely through the panels 820) can be provided within one or more portions of the planar members 820 as desired, for example, which can be shaped and sized as desired.

As will be described in FIGS. 18-21 below, the hubs, fluid conduits and transverse flanges (and optional vents) generally remain similar to at least one of the embodiments as described above, or for example, such that an end (or one of the male tips) of the embodiments as described above is generally similar in size, shape and functionality. Furthermore, the panels 820, 920 and 1020 are generally similarly oppositely-positioned and outwardly offset with respect to their respective fluid conduit 840, 940 and 1040.

Figure 18:
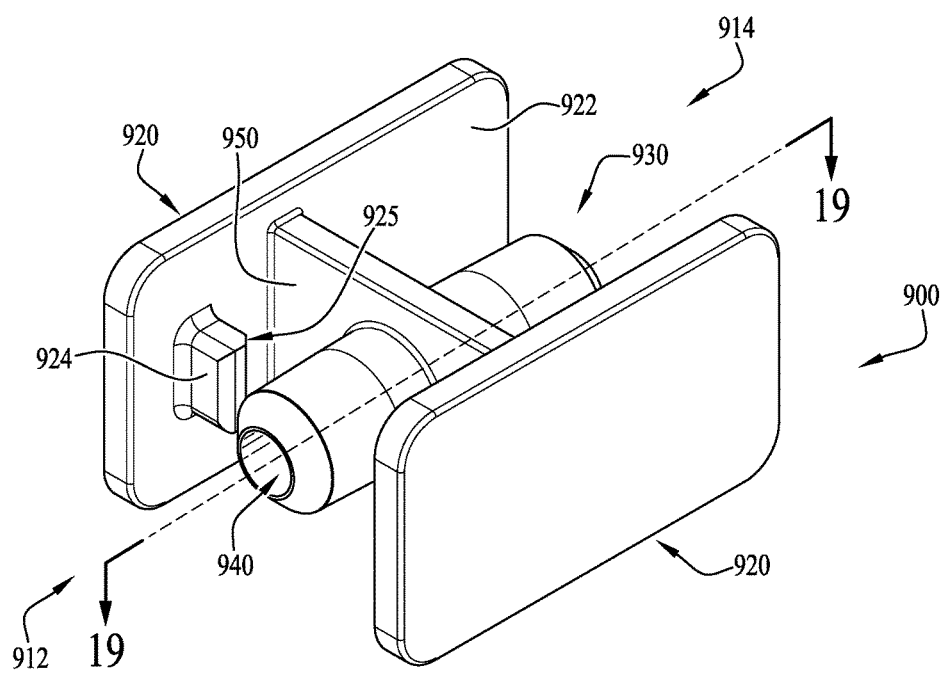
FIG. 18 is a perspective view of a syringe-to-syringe coupler according to another example embodiment of the present invention.
Figure 19:
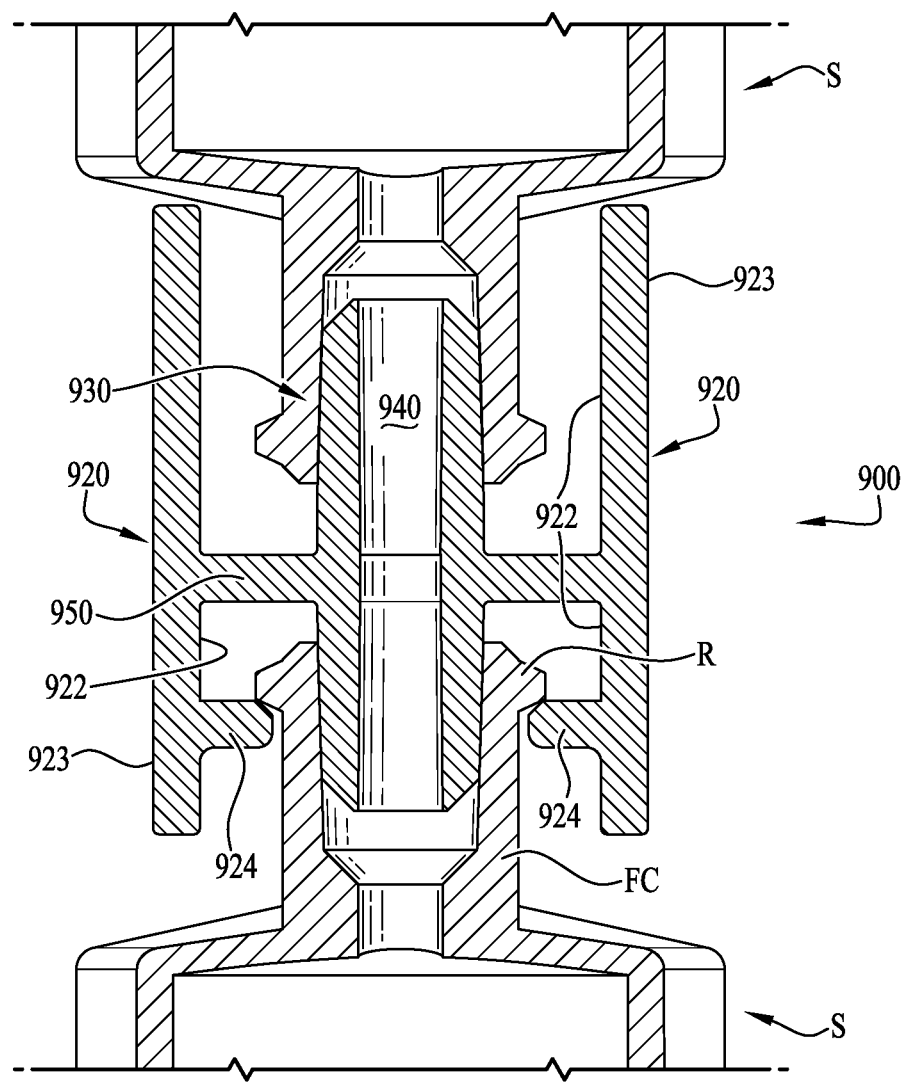
FIG. 19 is a cross-sectional view of the syringe-to-syringe coupler of FIG. 18, and showing a syringe coupling removably mounted to each end of the syringe-to-syringe coupler.

FIGS. 18-19 show a syringe-to-syringe coupler 900 according to another example embodiment of the present invention. The coupler 900 is configured to removably engage a first syringe S with a slip-fit coupling and removably engage a second syringe S with a removable coupling. The coupler 900 includes a hub 930, fluid conduit 940, flange 950 and gripping panels 920 of generally similar size and shape as the coupler 800 as described above. The coupler 900 comprises two fingers or extensions 924 extending from the inner face 922 of each of the panels 920. In example embodiments, the extensions 924 are configured for extending from the inner face 922 (and generally at the same position with respect to each other) such that the rib R on the female connector FC of the syringe S can be removably engaged with an underside or angled surface 925 of each of the extensions 924. Preferably, the surfaces 925 can be angled as desired, for example, to provide for appropriate removable engagement with the extensions 924. According to one example embodiment, only one of the inner surfaces 922 of the coupling 900 may include the extension 924, for example, such that it is only one of the ribs R of the female connector FC that is engaging the single extension.

Figure 20:
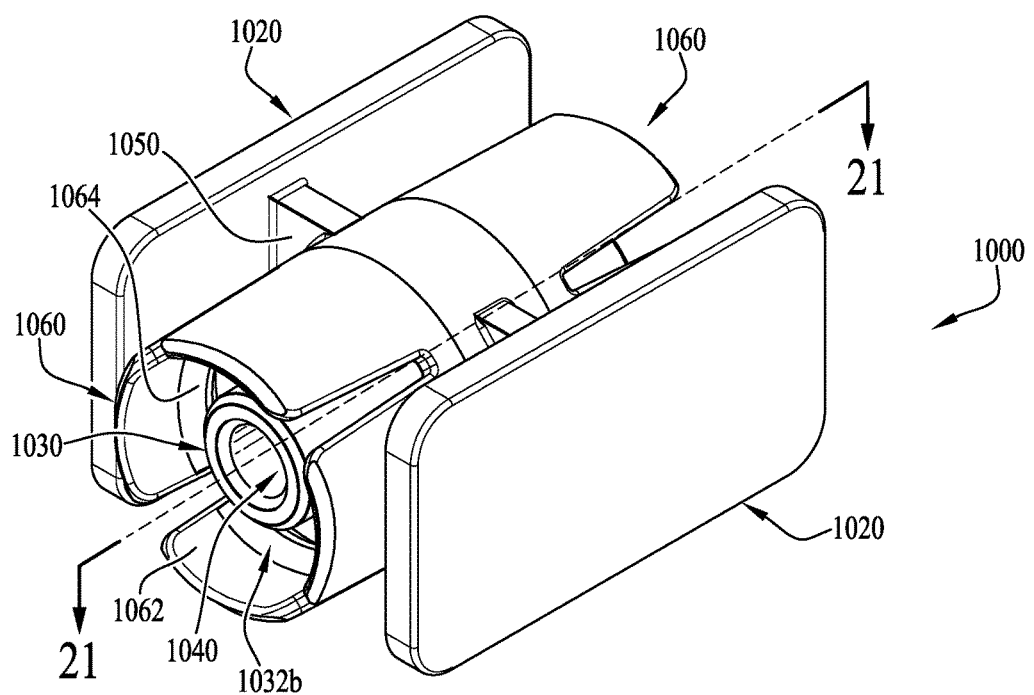
FIG. 20 is a perspective view of a syringe-to-syringe coupler according to another example embodiment of the present invention.
Figure 21:
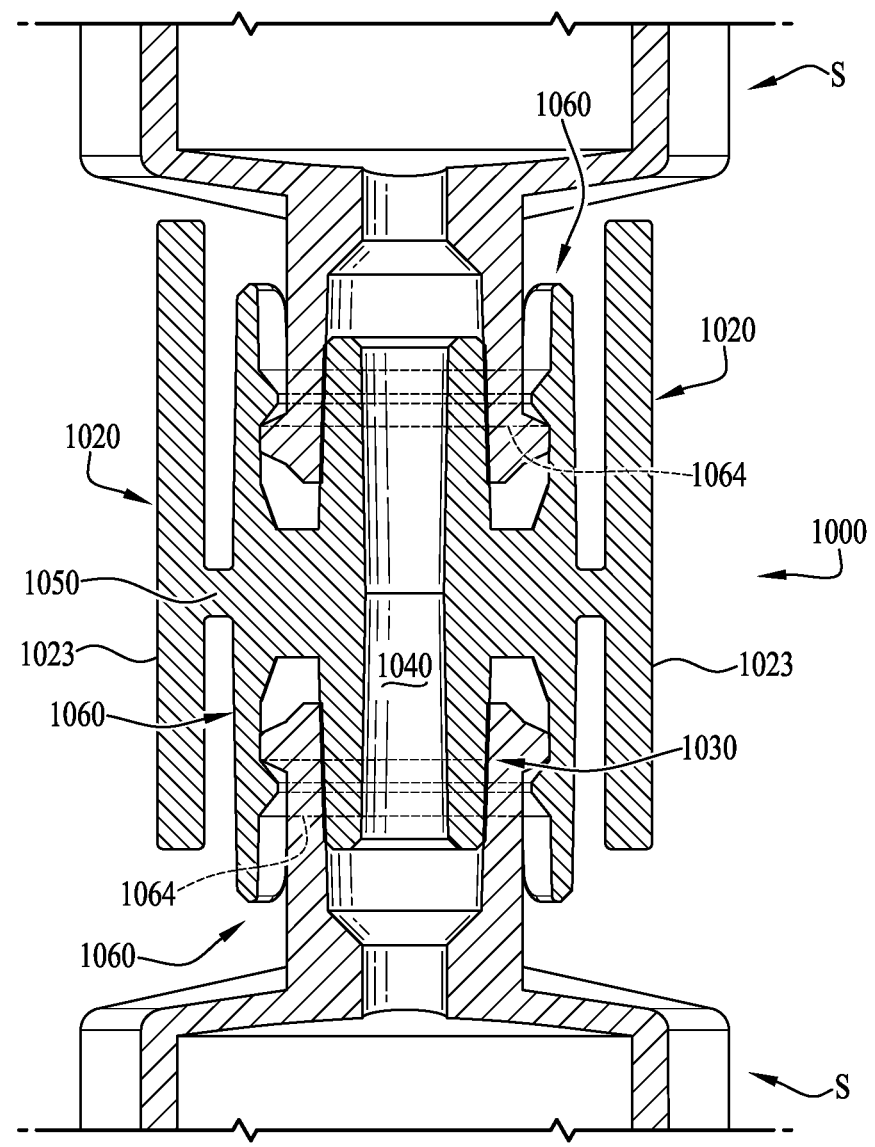
FIG. 21 is a cross-sectional view of the syringe-to-syringe coupler of FIG. 20, and showing a syringe coupling removably mounted to each end of the syringe-to-syringe coupler.

FIGS. 20-21 show a syringe-to-syringe coupler 1000 according to another example embodiment of the present invention. The coupler 1000 is substantially similar to the coupler 800 as described above, except that the coupler 1000 is configured to permanently engage two syringes S with threaded couplings, for example, rather than permitting removable engagement as provided by the threaded portions 864 of the coupler 800. The coupler 1000 includes a hub 1030, fluid conduit 1240, flange 1050 and gripping panels 1020 of similar size and shape as the coupler 800.

In example embodiments, the coupling element 1060 includes four tab members or clips 1062 extending from the central flange 1050 that generally form a circular array at a distance outwardly from the hub 1030 and generally extending from the midpoint of the hub toward the ends of the hub 1030. An internal portion or wall of at least one of the clips 1062 includes a rib 1064. In the depicted embodiment, each of the four clips 1062 comprise a rib 1064, for example, which remains in a substantially similar horizontal plane around the inner surfaces of each of the clips 1062 (see dashed lines of FIG. 21). In example forms, the female connector FC of each syringe S is generally installed by pushing the snap connection provided by the split collar and the rib R. In example embodiments, the clips are configured to prevent the female connector FC of the syringe S from being removed from the coupling element 1062. In example embodiments, the coupler 1000 is permanently attached to the syringe S, for example, since rotation provides no axial movement as the rib 1064 is substantially horizontal. Furthermore, the flexibility of the clips 1062 are configured for little to no flexibility, for example, such that the permanent coupling 1060 provides for a one-way coupling action. In example embodiments, the clips 1062 are configured for flexing just enough for the ribs R of the female connector FC to pass around the rib 1064, but the clips 1062 remain substantially rigid without much flexure such that the female connector FC remains substantially permanently coupled with the permanent connector 1060. In the depicted embodiment, the coupler 1000 further comprises a flange 1050 at the base of the coupling element 1060, which can comprise one or more vents 1066 extending through a portion thereof.

Figure 22:
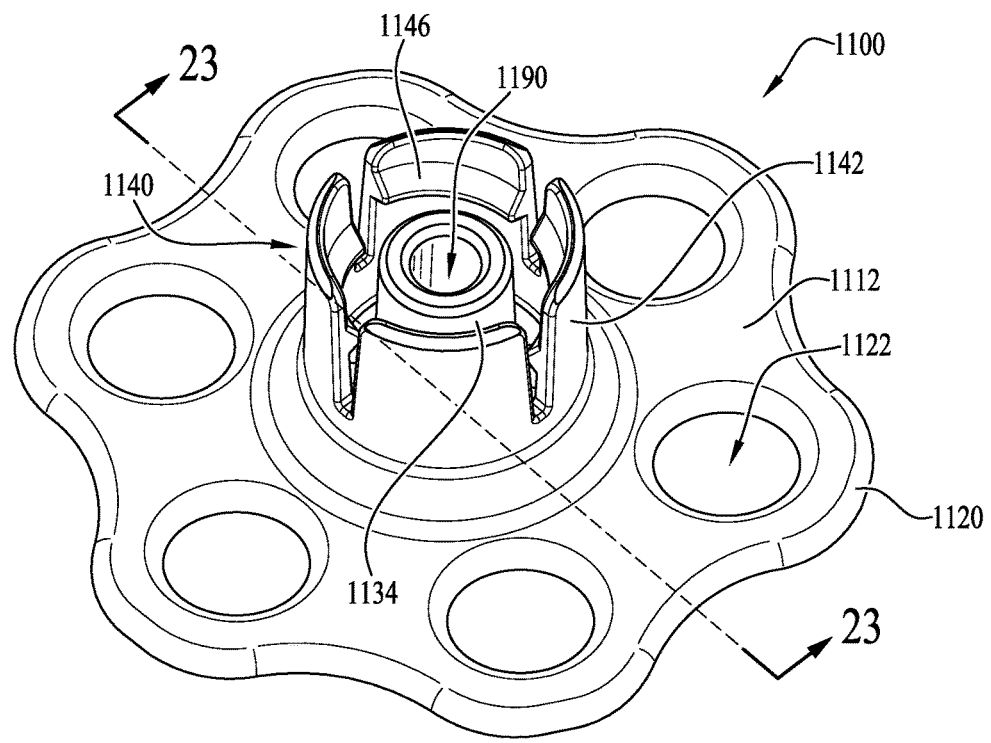
FIG. 22 is a perspective view of a tip cap according to an example embodiment of the present invention.
Figure 23:
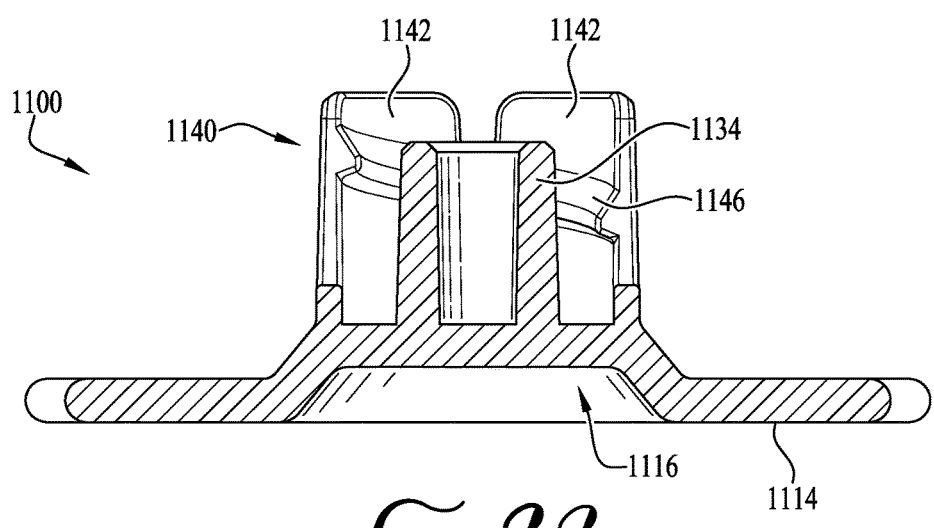
FIG. 23 is a cross-sectional view of the tip cap of FIG. 22 taken along line 23-23.

FIGS. 22-25 show a plurality of embodiments of a tip cap for engagement with the female connector FC of a syringe S according to example embodiments of the present invention. In example embodiments, the end caps as will be described herein can be configured for removable or permanent engagement with the ENFit compatible female connector FC, or for example, for removable or permanent engagement with a threaded tip TT. Preferably, as will be described below, the tip caps are choke resistant, for example, such that at least a portion thereof is dimensioned to prevent the caps from being swallowed by a child. FIGS. 22-23 show a tip cap 1100 according to one example embodiment of the present invention. As shown, the cap 1100 comprises an outer base or flange member 1112 and a coupling 1140 for providing engagement with the female connector FC of the syringe S. The base flange 1112 is generally shaped to comprise a wave-like, undulating pattern formed along an outer periphery of the flange 1112, for example, which generally moves along a radial path around the entirety of the flange 1112. In example embodiments, the outer periphery of the flange 1112 defines a plurality of outwardly radiused portions 1120 and a plurality of inwardly radiused portions 1121. In example embodiments, the radiused portions 1120, 1121 preferably act to provide a gripping or grasping surface, for example, to facilitate handling during installation and removal. In one example embodiment, one or more openings 1122 can be formed through the flange 1112 as desired, for example, that can provide additional gripping features in addition to air passageways to prevent the child from choking if the cap 1100 was inserted in its mouth. In the depicted embodiment, a circular array of six openings 1122 are formed in the flange 1112. In example embodiments, the coupling 1140 is generally centrally positioned at a central area of the flange 1112 and comprises four clips 1142 as similarly described above. In example embodiments, each of the clips 1142 can comprise thread portions 1146 formed on an internal portion thereof, for example, to provide for interengagement with the ribs R of the female connector FC. In some example embodiments, the central coupling 1134 can comprise an internal conduit 1190, for example, to permit insertion of a lumen extension tip of a syringe S (see FIG. 4).

In example embodiments, the flange 1112 comprises a substantially planar outer surface 1114 for permitting the cap 1100 to function as a stand to support the syringe S in a vertical orientation when the female connector FC is coupled with the coupling 1140. In example embodiments, a central recessed portion 1116 is generally formed adjacent the outer surface 1114. Preferably, increasing or decreasing the diameter and depth of the recessed portion 1116 controls the amount of surface area of the outer surface 1114 available to contact a support surface, table or other surface that the cap 1100 is resting on.

Figure 24:
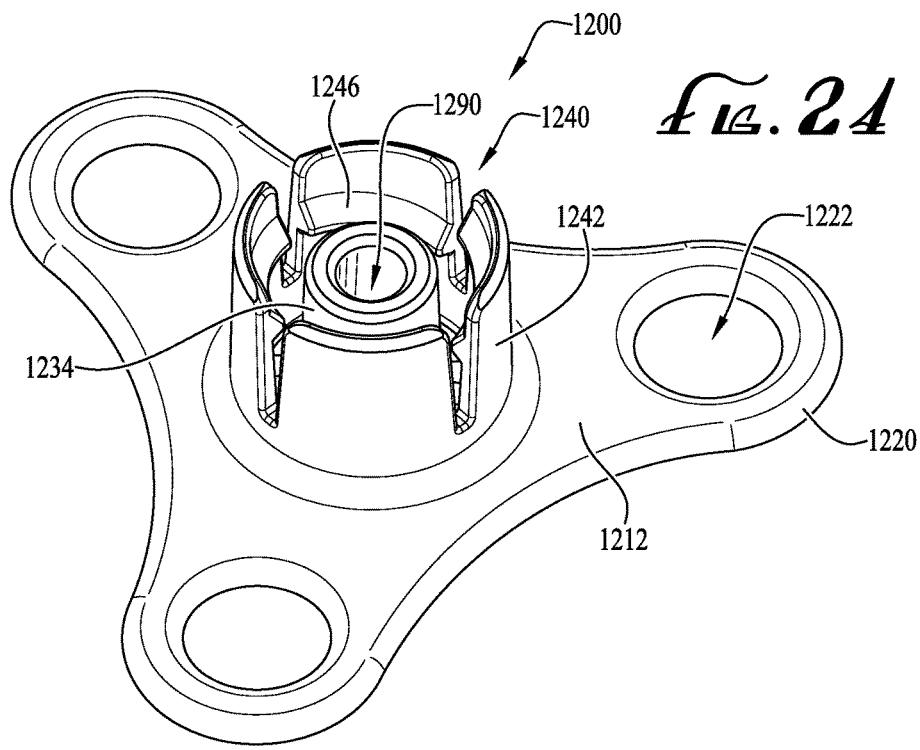
FIG. 24 is a perspective view of a tip cap according to another example embodiment of the present invention.
Figure 25:
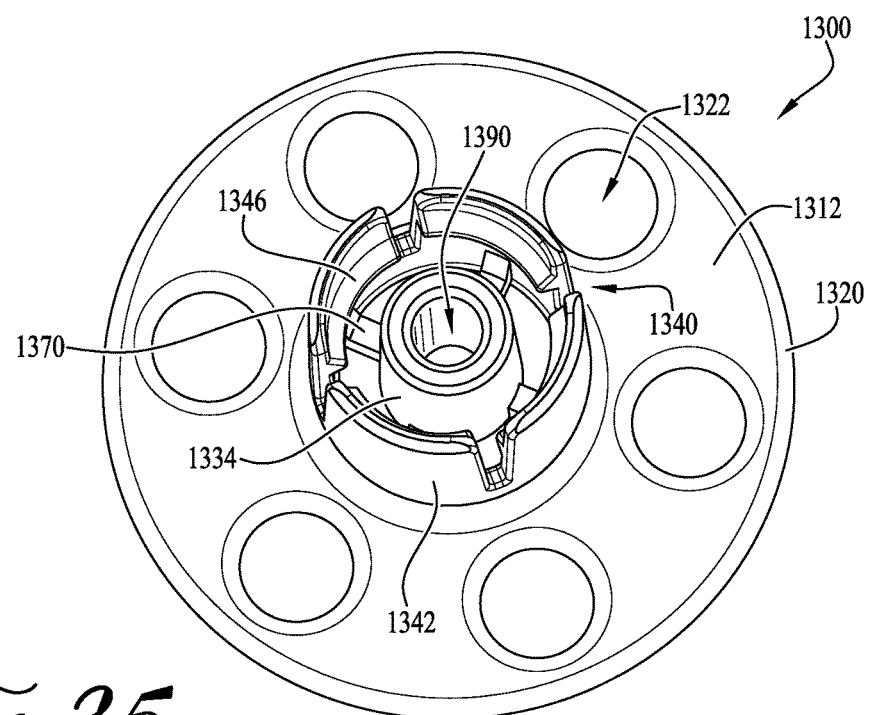
FIG. 25 is a perspective view of a tip cap according to another example embodiment of the present invention.

FIGS. 24-25 show tip caps 1200, 1300 according to additional example embodiments of the present invention. In example embodiments, the flanges 1212, 1312 can be shaped as desired, for example, generally triangular (see flange 1212) or substantially circular (see flange 1312). As shown in FIG. 24, the cap 1200 generally comprises the triangularly-shaped flange 1212, which comprises three openings 1222 extending therethrough, and the coupling 1240 generally centrally positioned at the center of the flange 1212. In example embodiments, an outer surface (not shown) permits the cap 1200 to rest atop a support surface, and when the female connector FC of a syringe S is connected thereto, the cap acts as a stand. As shown in FIG. 25, the flange 1312 is substantially circular or disc-shaped and comprises six openings 1322 formed therethrough. As similarly described above, the coupling 1340 is generally centrally positioned in the center of the flange 1312. In example embodiments and as described above, one or more tactile ribs or supports 1370 can be provided for engagement between the coupling 1334 and an inner portion of the clips 1342. Preferably, the tip caps 1100, 1200, 1300 can be shaped and sized as desired, and can act to support a syringe coupled thereto in a vertical orientation. Furthermore, the shape of the flange 1112, 1212 and 1312 and outer periphery thereof can be shaped as desired, for example, such that they are dimensioned to substantially, if not entirely, eliminate a child potentially choking if inserted into its mouth, and such that the an outer surface is provided for standing the coupled syringe in a vertical orientation.

Figure 26:
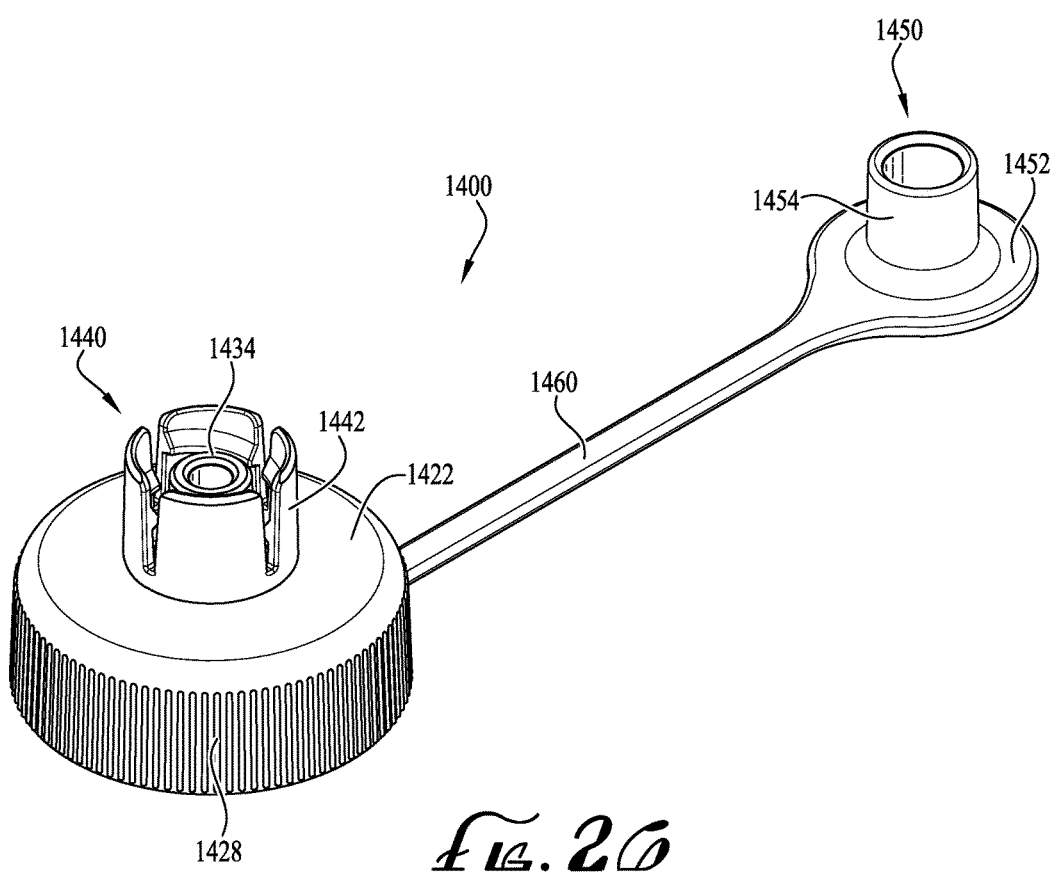
FIG. 26 is a perspective view of a fluid transfer connector according to another example embodiment of the present invention.

According to another example embodiment, the present invention relates to a fluid transfer lid 1400. As shown in FIG. 26, the fluid transfer lid 1400 comprises a generally circular top panel 22 with a coupling 1434 extending from a generally central position on the top panel 1422 outwardly in a first or distal direction. An attachment collar 1428 extends in a second or proximal direction from the top panel 1422, and an internal circumferential face thereof is threaded to releasably engage corresponding threads of a containment shell of a container. U.S. Published Patent Application 2016/0159635 discloses a fluid transfer lid for removably coupling to pharmacy bottles or containers for withdrawing and/or delivering liquid medication or other fluid therefrom or thereto, which is incorporated by reference herein for all purposes. An exterior circumferential face of the attachment collar 1428 of the fluid transfer lid 1400 optionally comprises spaced intentions, ridges, recesses, or other gripping features to assist a user in installing and removing the transfer lid onto and from the containment shell of the container. In example embodiments, a coupling 1440 is provided such that an array of four clips 1442 are positioned around the coupling 1434 for providing the dual action installation and removal mechanism for engagement with the female connector FC of the syringe S. Optionally, a port closure cap 1450 is attached to the fluid transfer lid 1400 by a tether 1460, which defines a flange or lip 1452 comprising a plug or cover (unshown) and a secondary cover or lip 1454 extending therefrom in the first direction. Preferably, the clips 1442 can comprise thread portions formed thereon, for example, as similarly described above. Furthermore, the clips can be configured for removable or permanent engagement.

Figure 27:
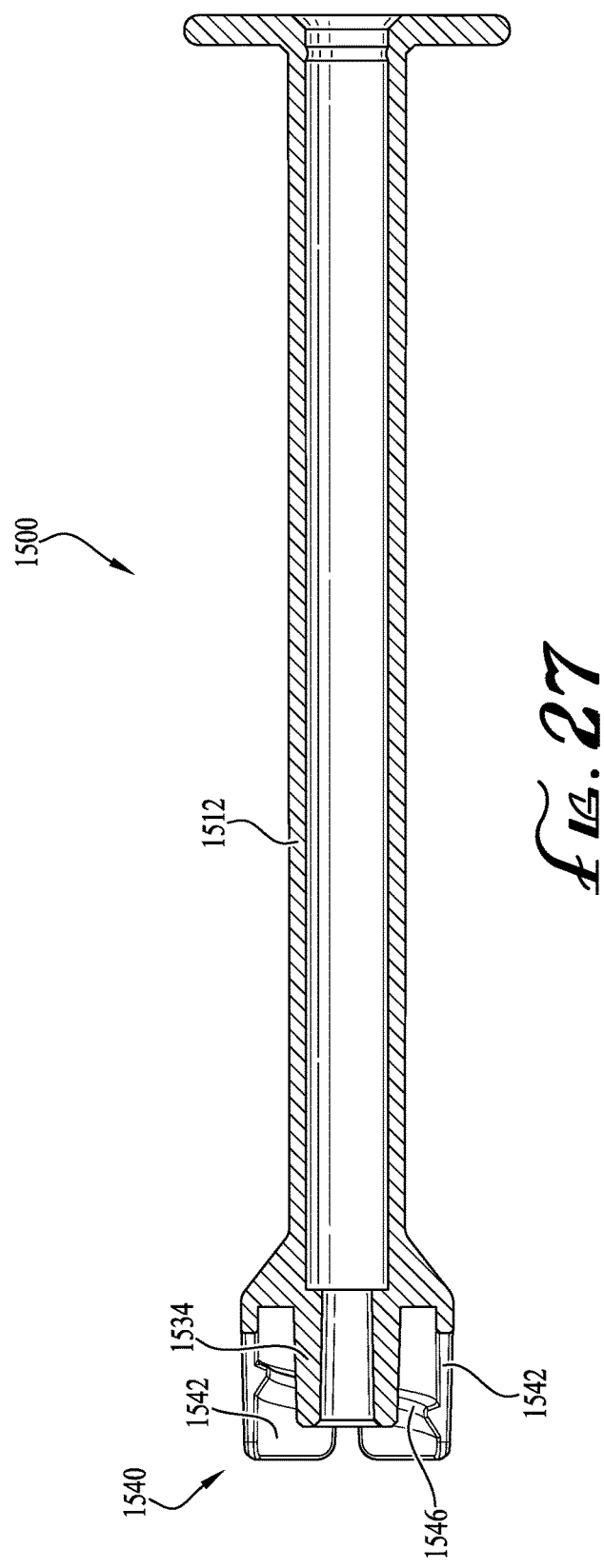
FIG. 27 is a cross-sectional view of a syringe according to another example embodiment of the present invention, and showing a coupling portion of the syringe comprising a plurality of clips for removable engagement with a coupling member.

FIG. 27 shows a syringe 1500 according to another example embodiment of the present invention. In example embodiments, the syringe 1500 comprises a modified male ENFit coupling substantially conforming to ISO design standard 80369-3, for example, rather than having a modified female ENFit coupling substantially conforming to ISO design standard 80369-3 (see syringe S as shown in FIGS. 4 and 10). As depicted, the syringe 1500 comprises a generally elongate and uniform barrel 1512 comprising a flange at one end and the modified male ENFit coupling at the other end. In example embodiments, the modified male ENFit coupling comprises the male coupling 1534, and a circular array of clips 1542 surrounding the coupling 1534. As similarly described above, the clips are preferably at least partially flexible to provide for engagement with a enteral connector, coupling, etc. comprising a female ENFit connector. Thread portions are optionally formed on an interior portion of the clips 1542 to provide for engagement with the female ENFit connector as described above.

In example forms, the couplings or clips as shown herein preferably provide for dual-action installation and removal, for example, such that the enteral couplings and other attachments/components can be more easily installed/removed with or from the female connector FC of the syringe S. Optionally, as described above, the coupling or clips can be configured for permanent engagement of the enteral coupling or attachments/components with the female connector FC of the syringe S. According to example forms, the enteral couplings or attachments/components generally comprise a radial array of 4 clips. Alternatively, three or less or more than four clips can be provided as desired. Optionally, the enteral connectors of the present invention can be configured for removable attachment with a threaded tip TT of a syringe.

While the invention has been described with reference to preferred and example embodiments, it will be understood by those skilled in the art that a variety of modifications, additions and deletions are within the scope of the invention, as defined by the following claims.

What is claimed is:

1. An enteral connector for coupling engagement with a female connector of a syringe, the enteral connector comprising:
a generally centrally-positioned coupling member axially extending along an elongate axis;
a circular array of tabs surrounding the coupling member and offset outwardly relative to the elongate axis of the coupling member, wherein at least one of the tabs comprises a thread portion inwardly extending therefrom, and wherein the thread portion is configured for removable connection with an outer rib of the female connector; and
a body surrounding the circular array of tabs.

2. The enteral connector of claim 1, wherein the circular array of tabs comprises four tabs wherein each tab of the four tabs comprises the thread portion inwardly extending therefrom, and wherein the thread portions are configured for removable coupling engagement with the outer rib of the female connector of the syringe.

3. The enteral connector of claim 2, wherein with the circular array of four tabs and thread portions formed thereon, the enteral connector is capable of providing a dual-action installation and removal mechanism such that a rotational and/or axial movement of one of the enteral connector or the female connector relative to the other of the enteral connector or the female connector provides for connecting or disconnecting one of the enteral connector or the female connector relative to the other of the enteral connector or the female connector.

4. The enteral connector of claim 3, wherein the enteral connector is configured to be removably coupled with the female connector by rotational movement of one of the enteral connector or the female connector relative to the other of the enteral connector or the female connector, wherein the thread portions of the four tabs are helical to accommodate a rotational connection and disconnection.

5. The enteral connector of claim 4, wherein the enteral connector is configured to be removably coupled with the female connector by axial movement of one of the enteral connector or the female connector relative to the other of the enteral connector or the female connector.

6. The enteral connector of claim 5, wherein the axial movement therebetween causes the outer rib to eventually interengage with the thread portions of the tabs, which causes to tabs to flex outwardly, thereby permitting the outer rib to pass by the thread portions.

7. The enteral connector of claim 5, wherein the enteral connector is in the form of a tip cap.

8. The enteral connector of claim 7, wherein the coupling member of the tip cap comprises an orifice formed therein for receiving a lumen extension tip of the female connector of the syringe.

9. The enteral connector of claim 7, wherein the tip cap comprises a flange for acting as a stand.

10. The enteral connector of claim 9, wherein the coupling member of the tip cap comprises an orifice formed therein for receiving a lumen extension tip of the female connector of the syringe.

11. The enteral connector of claim 7, wherein the tip cap is a self-righting tip cap.

12. The enteral connector of claim 5, wherein the enteral connector is in the form of a syringe-to-syringe coupler.

13. The enteral connector of claim 5, wherein the enteral connector is in the form of a fluid transfer lid.

14. The enteral connector of claim 1, wherein the circular array of tabs comprises a pair of partially flexible tabs oppositely opposed from each other and a pair of generally rigid guide tabs oppositely opposed from each other, and wherein the at least one tab comprising the thread portion inwardly extending therefrom is at least one of the partially flexible tabs.

15. The enteral connector of claim 14, wherein the thread portion of the at least one partially flexible tab is configured for engagement with a rib formed on an outer portion of the female connector when the female connector is connected with the coupling member.

16. The enteral connector of claim 15, wherein the enteral connector is permanently coupled with the female connector by axial movement of one of the enteral connector or the female connector relative to the other of the enteral connector or the female connector, whereby axial coupling engagement of the female connector of the syringe with the coupling member causes the partially flexible tabs to flex outwardly to a flexed state, permitting the rib to pass by the thread portion, and returning to a neutral state whereby the rib of the female connector is engaged with the thread portion and preventing disconnection between the female connector and the enteral connector.

17. The enteral connector of claim 14, wherein the guide tabs prevent rotation of the female connector relative to the coupling member by interference between the guide tabs and ribs formed on an outer surface portion of the female connector.

18. The enteral connector of claim 1, wherein the enteral connector is configured to couple with an ISO 80369-3 compatible female connector.

19. The enteral connector of claim 1, wherein the enteral connector is configured to couple with a female connector comprising a threaded tip.

* * * * *